US011259908B2

(12) United States Patent
Marr et al.

(10) Patent No.: US 11,259,908 B2
(45) Date of Patent: Mar. 1, 2022

(54) ANIMAL INTRANASAL ADMINISTRATION DEVICE, SYSTEMS, AND ASSOCIATED METHODS

(71) Applicants: ELANCO US INC., Greenfield, IN (US); BOVICOR PHARMATECH INC., Vancouver (CA)

(72) Inventors: Amy L. Marr, Greenfield, IN (US); Jane Granville Owens, Greenfield, IN (US); Jeffrey Kyle Hill, Greenfield, IN (US); Casey J. Strange, Greenfield, IN (US); Randall Lee Waln, Greenfield, IN (US); Christopher C. Miller, North Vancouver (CA); Gilly Regev-Shoshani, Vancouver (CA); Alex Stenzler, Long Beach, CA (US); Steve Han, Huntington Beach, CA (US)

(*) Notice: Subject to any disclaimer, the term of this patent is extended or adjusted under 35 U.S.C. 154(b) by 492 days.

(21) Appl. No.: 16/319,229

(22) PCT Filed: Jul. 19, 2017

(86) PCT No.: PCT/US2017/042874
§ 371 (c)(1),
(2) Date: Jan. 18, 2019

(87) PCT Pub. No.: WO2018/017722
PCT Pub. Date: Jan. 25, 2018

(65) Prior Publication Data
US 2020/0297468 A1  Sep. 24, 2020

Related U.S. Application Data

(60) Provisional application No. 62/364,808, filed on Jul. 20, 2016.

(51) Int. Cl.
*A61D 7/04* (2006.01)
*A61M 15/08* (2006.01)

(52) U.S. Cl.
CPC .............. *A61D 7/04* (2013.01); *A61M 15/085* (2014.02); *A61M 2202/0275* (2013.01); *A61M 2250/00* (2013.01)

(58) Field of Classification Search
CPC .. A01K 1/0157; A01K 1/0236; A01K 1/0263; A01K 15/00; A61B 17/12031;
(Continued)

(56) References Cited

U.S. PATENT DOCUMENTS 3,788,296 A    1/1974  Klatt et al.
4,491,089 A *  1/1985  Kelly .................. B66F 3/35
                                                 119/722
(Continued)

FOREIGN PATENT DOCUMENTS

CN    2155888 Y     2/1994
CN    101198368 A   6/2008
(Continued)

OTHER PUBLICATIONS

International Preliminary Report on Patentability received for PCT Patent Application No. PCT/US2017/042874, dated Jan. 31, 2019, 10 pages.
(Continued)

*Primary Examiner* — Annette Dixon
(74) *Attorney, Agent, or Firm* — Faegre Drinker Biddle & Reath LLP

(57) ABSTRACT

A veterinary subject intranasal administration device includes a first support member portion including a septum interface portion sized for insertion into a nasal passage of the veterinary subject; an actuation mechanism connected to the first support member portion; and a fluid conduit having a distal end opposite a supported end, the distal end sized for insertion into the nasal passage of the veterinary subject, the fluid conduit being flexible and configured to receive fluid
(Continued)

from a fluid source and discharge the fluid through the distal end into the nasal passage, the distal end of the fluid conduit being unsupported and movable relative to the septum interface portion.

28 Claims, 19 Drawing Sheets

(58) Field of Classification Search
CPC .......... A61B 17/1204; A61B 17/12099; A61B 17/12104; A61B 17/12136; A61B 17/12159; A61B 17/12181; A61B 17/24; A61K 33/00; A61K 9/0043; A61K 9/007; A61M 11/00; A61M 13/003; A61M 15/0028; A61M 15/0068; A61M 15/0081; A61M 15/085; A61M 16/0459; A61M 16/0461; A61M 16/0479; A61M 16/0486; A61M 16/0605; A61M 16/0672; A61M 16/0683; A61M 16/085; A61M 16/0875; A61M 16/12; A61M 2016/0039; A61M 2016/1035; A61M 2025/0226; A61M 2202/0275; A61M 2205/073; A61M 2210/0618; A61M 2230/005; A61M 2230/432; A61M 25/02; A61M 31/00; B66F 3/35; Y10S 128/26; Y10S 128/911; Y10S 128/912
See application file for complete search history.

(56) References Cited

U.S. PATENT DOCUMENTS

| | | | | |
|---|---|---|---|---|
| 4,886,493 | A * | 12/1989 | Yee | A61M 11/00 604/516 |
| 5,097,827 | A * | 3/1992 | Izumi | A61M 25/02 128/200.26 |
| 5,513,635 | A | 5/1996 | Bedi | |
| 6,398,774 | B1 * | 6/2002 | Penner | A61M 15/0028 604/48 |
| 6,432,077 | B1 | 8/2002 | Stenzler | |
| 6,668,828 | B1 | 12/2003 | Figley et al. | |
| 6,818,669 | B2 | 11/2004 | Moskowitz et al. | |
| 7,122,018 | B2 | 10/2006 | Stenzler et al. | |
| 7,335,181 | B2 | 2/2008 | Miller et al. | |
| 7,481,219 | B2 | 1/2009 | Lewis et al. | |
| 7,516,742 | B2 | 4/2009 | Stenzler et al. | |
| 8,518,457 | B2 * | 8/2013 | Miller | A61K 9/007 424/718 |
| 9,265,922 | B2 * | 2/2016 | Barbut | A61B 17/12136 |
| 10,220,174 | B2 * | 3/2019 | Huerta | A61M 16/0875 |
| 10,987,377 | B2 * | 4/2021 | Murray | A61K 9/007 |
| 2003/0079749 | A1 | 5/2003 | Strickland et al. | |
| 2004/0016432 | A1 | 1/2004 | Genger et al. | |
| 2004/0081580 | A1 | 4/2004 | Hole et al. | |
| 2005/0279351 | A1 | 12/2005 | Lewis | |
| 2007/0086954 | A1 | 4/2007 | Miller | |
| 2007/0104653 | A1 | 5/2007 | Miller et al. | |
| 2009/0196930 | A1 | 8/2009 | Surber et al. | |
| 2012/0003293 | A1 | 1/2012 | Miller et al. | |
| 2012/0209096 | A1 | 8/2012 | Jaffe et al. | |
| 2014/0251340 | A1 | 9/2014 | Pastoor | |
| 2015/0157657 | A1 | 6/2015 | Stenzler et al. | |
| 2015/0297782 | A1 | 10/2015 | Miller et al. | |
| 2016/0051579 | A1 | 2/2016 | Stenzler et al. | |
| 2016/0235512 | A1 | 8/2016 | Miller et al. | |
| 2017/0151277 | A1 | 6/2017 | Miller et al. | |

FOREIGN PATENT DOCUMENTS

| | | |
|---|---|---|
| CN | 203220674 U | 10/2013 |
| EP | 1968684 | 2/2016 |
| JP | S58-142023 U | 8/1983 |
| JP | S58142023 | 9/1983 |
| JP | 2014-530708 A | 11/2014 |
| JP | 2014530708 | 11/2014 |
| WO | 2013057672 | 4/2013 |

OTHER PUBLICATIONS

International Search Report for PCT/US2017/042874 filed on Jul. 19, 2017 dated Oct. 11, 2017, 7 pages.
Written Opinion of the International Searching Authority for PCT/US2017/042874 filed on Jul. 19, 2017, 10 pages.
Official Action for Russian Application No. 2019104088, dated Dec. 9, 2019, 4 pages.
Official Action for Japanese Application No. 2019-524129 dated Feb. 4, 2020, 2 pages.

* cited by examiner

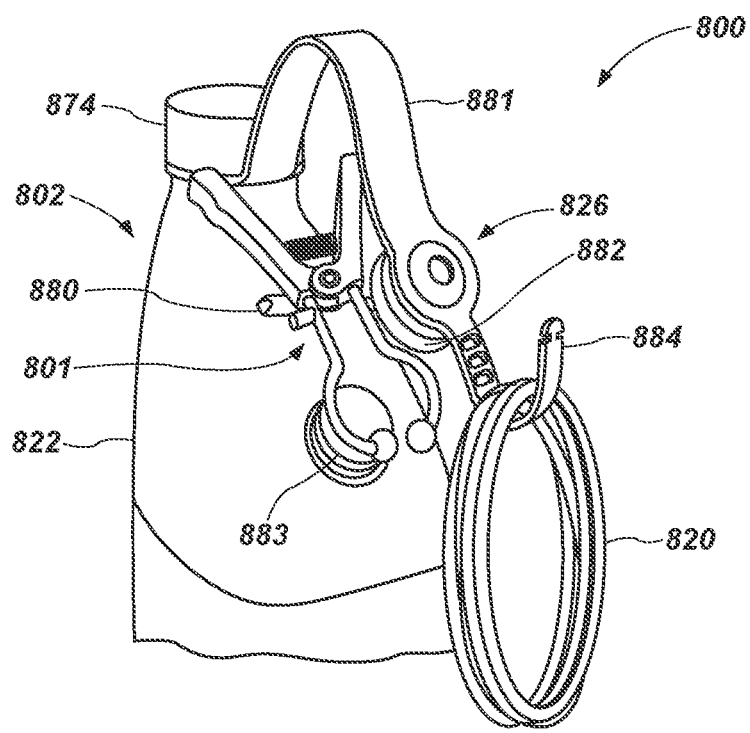
FIG. 6A
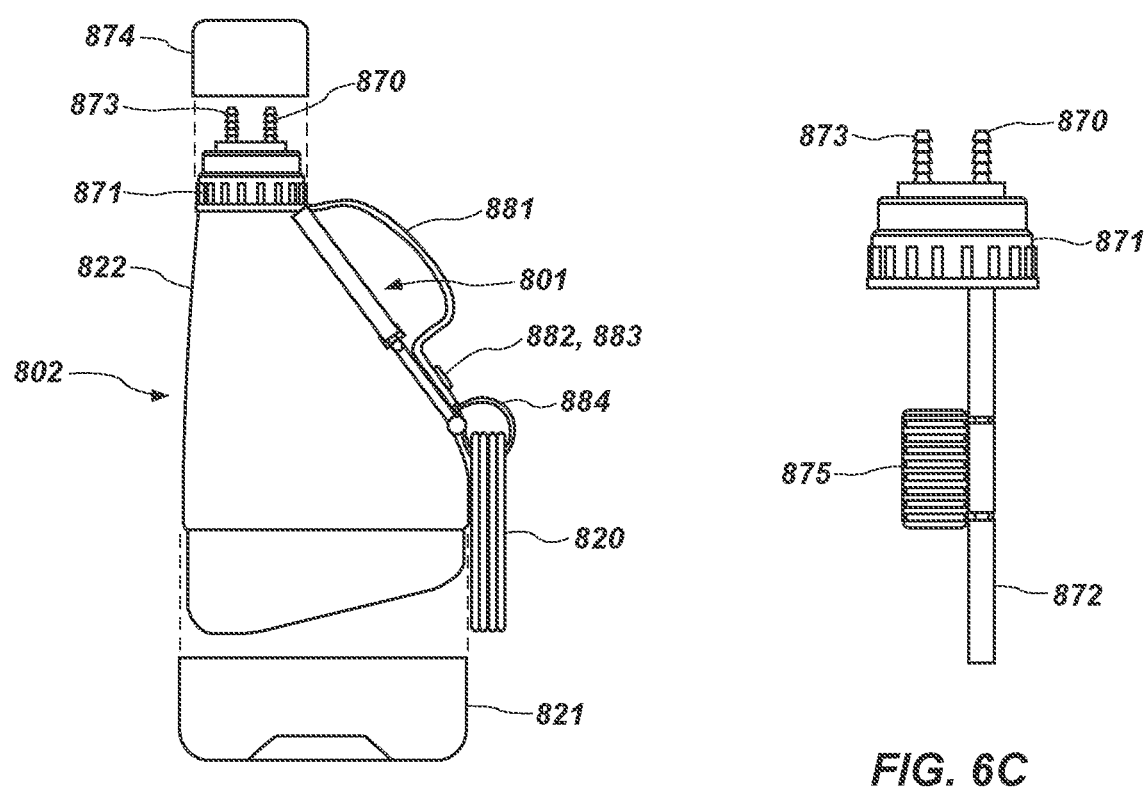
FIG. 6B
FIG. 6C

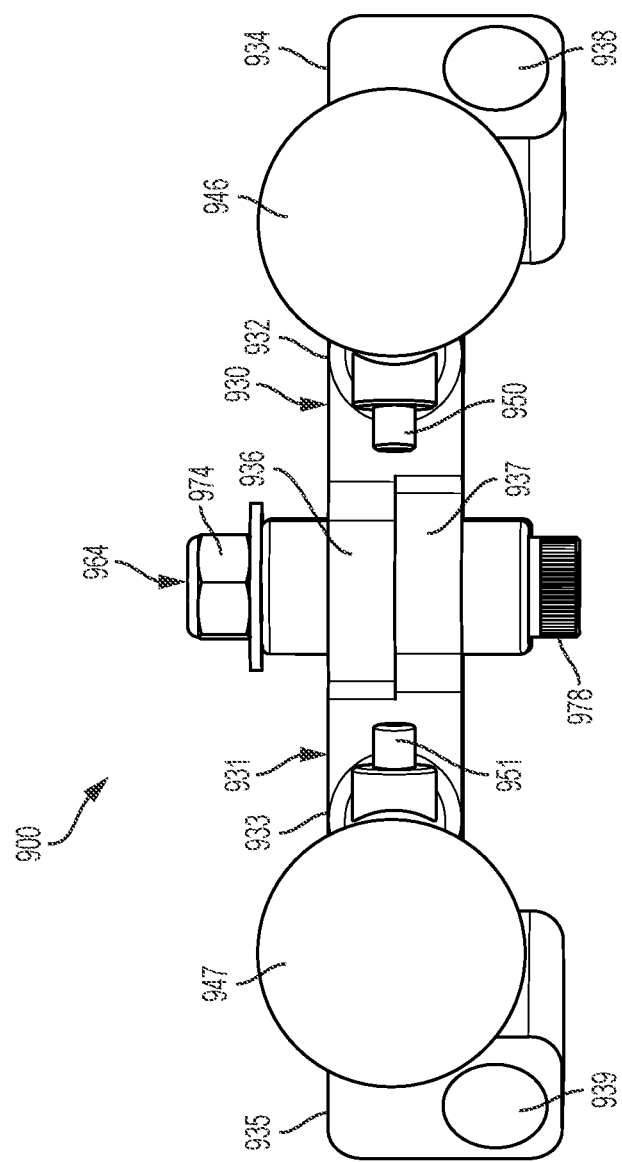

ANIMAL INTRANASAL ADMINISTRATION DEVICE, SYSTEMS, AND ASSOCIATED METHODS

CROSS-REFERENCE TO RELATED APPLICATIONS

This application is U.S. national stage application filed under 35 U.S.C. § 371 of International Application No. PCT/US2017/042874, filed Jul. 19, 2017, which claims the benefit of U.S. Pat. Appl. No. 62/364,808, filed Jul. 20, 2016, both applications incorporated by reference in their entirety.

BACKGROUND OF THE DISCLOSURE

Nitric oxide gas has an antimicrobial effect and when safely administered can be used as a therapeutic treatment of microbial infection in a subject. While many systems have been described for the use of nitric oxide in clinical settings, these systems are designed for the delivery of nitric oxide gas to the subject in a way that requires the subject to remain stationary for an extended period of time. Unfortunately, many instances where treatment of nitric oxide would be particularly beneficial do not allow for the subject to be stationary or immobilized for the length of time needed to receive an effective dosage of nitric oxide gas.

For example, one such instance is in the cattle industry, where Bovine Respiratory Disease Complex (BRDc) continues to be the most common disease in feeder beef cattle in North America, affecting 20-40% of receiver calves annually. Production losses from BRDc include respiratory morbidity and mortality as well as increased treatment and processing cost. Its pathogenicity has been linked to a primary viral infection followed by a secondary bacterial infection.

While the incidence of BRDc has been shown to be reduced in animals treated with a suitable dosage of nitric oxide gas, effective commercialization of such therapy remains infeasible due to administration time constraints. Accordingly, there exists a need for a device, system, and method to quickly and efficiently deliver an effective dose of a nitric oxide gas.

The background of the disclosure is described herein to explain the context of the present invention. This is not to be taken as an admission or a suggestion that any of the material referred to was published, known or part of the common general knowledge in the art to which the present invention pertains, in the United States or in any other country, as at the priority date of any of the claims.

SUMMARY OF THE DISCLOSURE

In one aspect, devices for intranasal administration of fluids are provided. In some embodiments, an intranasal administration device for a veterinary subject comprises a first support member portion including a septum interface portion sized for insertion into a nasal passage of the veterinary subject; an actuation mechanism connected to the first support member portion; and a fluid conduit having a distal end opposite a supported end, the distal end sized for insertion into the nasal passage of the veterinary subject, the fluid conduit being flexible and configured to receive fluid from a fluid source and discharge the fluid through the distal end into the nasal passage, the distal end of the fluid conduit being unsupported and movable relative to the septum interface portion.

In some embodiments, an intranasal administration device for a veterinary subject comprises a first member pivotally coupled to a second member, each of the first member and the second member including an arm, wherein the arm of the first member is pivotally coupled to the arm of the second member; a handle portion coupled to and extending proximally from the arm; and a jaw coupled to and extending distally from the arm and having a distal end, wherein the distal end of the jaw of the first member and the distal end of the jaw of the second member are configured to clamp the nasal septum of a veterinary subject; a fluid conduit supported by the first member and having a distal end detached from the distal end of the jaw of the first member; and a second fluid conduit supported by the second member and having a distal end detached from the distal end of the jaw of the second member. When the intranasal administration device is clamped to the nasal septum the first fluid conduit and the second fluid conduit extend past a flow constriction formed by the alar folds and the basal folds of the veterinary subject to deliver a fluid into the veterinary subject.

In another aspect, a method to deliver a fluid intranasally to a veterinary subject is provided. In some embodiments, the method comprises opening jaws of an intranasal administration device, the intranasal administration device comprising fluid conduits; inserting the jaws and the fluid conduits into the nostrils of the veterinary subject; clamping the nasal septum of the veterinary subject with the jaws to retain the fluid conduits in the nose of the veterinary subject; and discharging a fluid through the fluid conduits. The animal intranasal administration device can include a first support member pivotally coupled to a second support member, each of the first support member and the second support member including an arm, wherein the arm of the first support member is pivotally coupled to the arm of the second support member; a handle portion coupled to and extending proximally from the arm; a jaw coupled to and extending distally from the arm, wherein the jaw of the first support member and the jaw of the second support member are configured to clamp the nasal septum of an animal; a first fluid conduit supported by the first support member and having a distal end; and a second fluid conduit supported by the second support member and having a distal end, wherein when the animal intranasal administration device is clamped to the nasal septum the first fluid conduit and the second fluid extend past a flow constriction formed by the alar fold and the basal fold of the animal to deliver a fluid into the nasopharynx of the animal.

There has thus been outlined, rather broadly, various features of the invention so that the detailed description thereof that follows may be better understood, and so that the present contribution to the art may be better appreciated. Other features of the present invention will become clearer from the following detailed description taken with the accompanying claims.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIGS. 6A-6C illustrate aspects of an animal intranasal administration system, in accordance with a further example of the present disclosure.

FIG. 12 is a rear view of the intranasal administration device depicted in FIG. 7.

Figure 1:
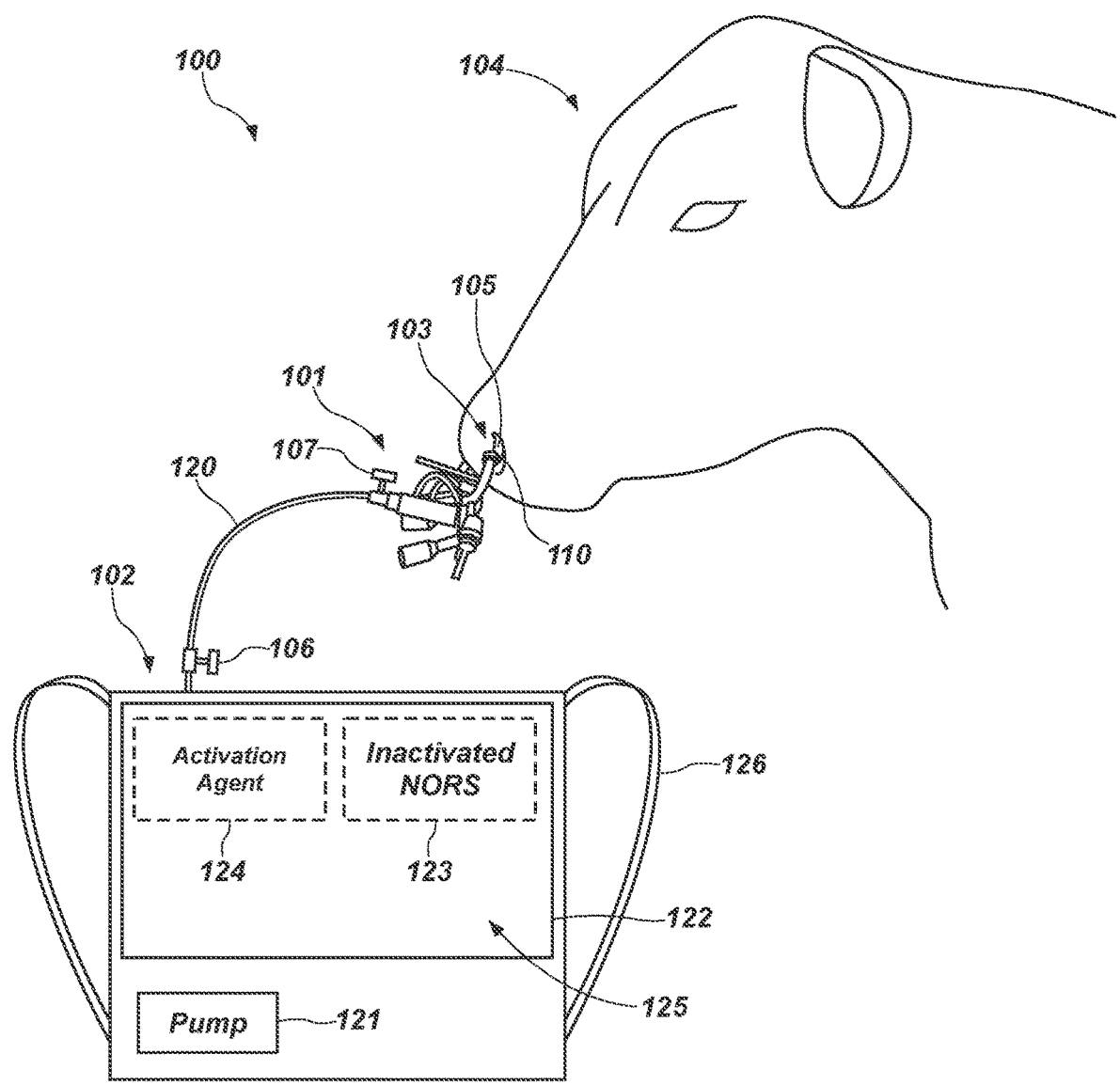
FIG. 1 is a schematic illustration of an animal intranasal administration system, in accordance with an example of the present disclosure.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplifications set out herein are not to be construed as limiting the scope of the invention in any manner.

DETAILED DESCRIPTION

Each of the following terms has the meaning associated with it in this section.

"About" as used herein when referring to a measurable value such as an amount, a temporal duration, and the like, is meant to encompass variations of ±20%, ±10%, ±5%, ±1%, and ±0.1% from the specified value, as such variations are appropriate. It is to be understood that in the present specification, the use of the term "about" in connection with a numerical value also affords support for the exact numerical value as though it had been recited without the term "about".

The terms "comprises," "comprising," "containing," and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

Except where a contrary intent is expressly stated, terms are used in their singular form for clarity and are intended to include their plural form.

"NORS" as used herein may refer to a nitric oxide releasing solution or substance. In one aspect, NO released from NORS may be a gas.

As used herein, "gaseous nitric oxide," or "gNO" refers to exogenous nitric oxide. gNO can be delivered to a veterinary subject per se, or can be delivered via NORS.

The term "veterinary subject" refers to a non-human animal or individual. Some non-limiting examples of veterinary subjects can include a bovine, goat, swine, foul, canine, feline, horse, bison, alpaca, llama, sheep, and the like. In one embodiment, the veterinary subject can be a bovine. In another embodiment, the veterinary subject can be a chicken, rooster, duck, goose, pheasant, or other fowl. In another embodiment, the veterinary subject can be a pig or other swine. In another embodiment, the veterinary subject can be a dog or a cat. In another embodiment, the veterinary subject can be a ferret or a mink. In yet another embodiment, the veterinary subject can be a commercially salable animal.

Occurrences of the phrase "in one embodiment," or "in one aspect," herein do not necessarily all refer to the same embodiment or aspect.

As used herein a "therapeutic agent" refers to an agent that can have a beneficial or positive effect on a veterinary subject when administered to the veterinary subject in an appropriate or effective amount. In one aspect, NO can be a therapeutic agent.

As used herein, an "effective amount" of an agent is an amount sufficient to accomplish a specified task or function desired of the agent. The phrase "therapeutically effective amount," as used herein, refers to an amount that is sufficient or effective to prevent or treat (delay or prevent the onset of, prevent the progression of, inhibit, decrease or reverse) a disease or disorder in a subject. It is understood that various biological factors may affect the ability of a substance to perform its intended task. Therefore, a "therapeutically effective amount" may be dependent in some instances on such biological factors. Further, while the achievement of therapeutic effects may be measured by veterinarian, or other qualified veterinary personnel using evaluations known in the art, it is recognized that individual variation and response to treatments may make the achievement of therapeutic effects a somewhat subjective decision. The determination of an effective amount or therapeutically effective amount is well within the ordinary skill in the art of pharmaceutical sciences and medicine.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

In one aspect, the present disclosure provides an animal intranasal administration device, and associated systems and methods related to a nitric oxide releasing solution (NORS) capable of reducing the presence of a bacteria, virus, or other pathogen in a veterinary subject. In one aspect, the present disclosure provides a method and apparatus for treating a subject animal with the delivery of a nitric oxide releasing solution to a treatment site of the veterinary subject, such as at least a portion of an upper respiratory tract of the animal.

The present disclosure allows for delivery of nitric oxide to an ambulatory veterinary subject, or to an assembly line of veterinary subjects where the administration protocol for delivery of the nitric oxide releasing solution is accomplished in a short time period. For example, the extended release and delivery of nitric oxide to the treatment site by way of the administered nitric oxide releasing solution allows for the treated subject to remain ambulatory during treatment, or stationary for a very short period of time. Thus, the veterinary subject is not constrained to a nitric oxide delivery device during the entire duration of nitric oxide delivery. Rather, the nitric oxide releasing solution can be administered to the subject over a short duration of treatment, and following administration the nitric oxide releasing solution will continue to deliver an extended release of a therapeutically effective amount of nitric oxide to the subject. The ability for the subject to remain ambulatory during treatment is particularly important in cattle, because cattle or other veterinary subjects can become stressed when they are restrained, such as in a squeeze chute, and stress can exacerbate and increase the incidence of BRDc. In some embodiments, for example in connection with companion animals, it may be desirable to guide the fluid conduits without the animal fully supporting the intranasal administration device. Instead, the animal's head may be held while the fluid conduits are inserted until the depth stop surface contacts the nose of the animal and the fluid is discharged, at which time the device can be removed.

In certain embodiments, the nitric oxide releasing solution is prepared just prior to administration to the subject through the administration of an acidifying or activation agent (e.g., citric acid) to a dormant NORS solution. Alternatively, a sodium nitrite can be administered to a dormant acidified solution. Either mechanism can be selected and used based on a number of performance factors such as most stable shelf life, etc. For example, administration of the acidifying agent to the dormant solution results in the lowering of the pH of the dormant solution, thereby activating the nitric oxide releasing solution to be administered to the treatment site. Importantly, the nitric oxide releasing solution can provide for extended production of nitric oxide, for example, beyond the time required to administer the nitric oxide releasing solution. In one embodiment, the nitric oxide releasing solution produces nitric oxide for a period of between 1 minute and 24 hours. In one embodiment, the nitric oxide releasing solution produces nitric oxide for a period of between 10 and 45 minutes. In one embodiment, the nitric oxide releasing solution produces nitric oxide for at least 15 minutes. In one embodiment, the nitric oxide releasing solution produces nitric oxide for at least 30 minutes. In another embodiment, the nitric oxide releasing solution produces nitric oxide for at least 1 hour. In another embodiment, the nitric oxide releasing solution produces nitric oxide for at least 4 hours. In another embodiment, the nitric oxide releasing solution produces nitric oxide for at least 8 hours. In another embodiment, the nitric oxide releasing solution produces nitric oxide for at least 12 hours. In another embodiment, the nitric oxide releasing solution produces nitric oxide for at least 24 hours. Thus, the administered nitric oxide releasing solution provides for continuous delivery of nitric oxide to the treatment site of the subject. It should be noted that in some embodiments, the treatment site can be at or near the location of NORS administration, for example, the upper respiratory tract. However, in some embodiments, the treatment site (i.e. the location where nitric oxide therapy is desired) can be distal from the location of NORS administration (e.g. the lower respiratory tract).

The nitric oxide releasing solution may be administered to the subject in a variety of forms. The nitric oxide releasing solution may be administered as a liquid, a spray, a vapor, micro-droplets, mist, or any form which provides the release of nitric oxide from the solution, as would be understood by one skilled in the art. In one embodiment, the nitric oxide releasing solution is administered as a spray. In another embodiment, the nitric oxide releasing solution is administered as a vapor. In another embodiment, the nitric oxide is administered as a gas. The amount or dosing volume of administered nitric oxide releasing solution may be varied in order to optimize the duration of nitric oxide production and delivery. In one embodiment, the amount of nitric oxide releasing solution administered to a subject is between about 0.1 mL and 5000 mL. In another embodiment, the amount of nitric oxide releasing solution administered to a subject is between about 10 mL and 1000 mL. In one embodiment, the amount of nitric oxide releasing solution administered to a subject is about 2 mL. In one embodiment, the amount of nitric oxide releasing solution administered to a subject is about 10 mL. In one embodiment, the amount of nitric oxide releasing solution administered to a subject is about 32 mL. In another embodiment, the amount of nitric oxide releasing solution administered to a subject is about 160 mL. These amounts or others may be administered in a single spray or in multiple sprays (e.g. 2, 3, 4, 5, 6, or 8-10 sprays) within a given dosage time, for example within 1 minute, 30 seconds, 10 seconds, 5 seconds, 2 seconds, or any other window deemed suitable or beneficial for administering single or multiple sprays. The nitric oxide releasing solution may be readministered one or more times, as necessary to effectively treat the subject. In one embodiment, the nitric oxide releasing solution is administered once to a subject. In another embodiment, the nitric oxide releasing solution is administered multiple times to a subject, where the nitric oxide releasing solution is readministered substantiantially after completion of the extended release of nitric oxide gas from the prior dosage administered.

In certain embodiments, nitric oxide releasing solution is directly administered into the upper respiratory tract of the subject. For example, in one embodiment, the nitric oxide releasing solution is sprayed into the upper respiratory tract of the subject. The solution may be administered into the upper respiratory tract of the subject once an hour, once a day, once a week, once every two weeks, once a month, once every two months, once a year, and any and all ranges therebetween as required to treat the subject. In one embodiment, the solution is sprayed once a week. In another embodiment, the solution is sprayed once a week for four consecutive weeks. The nitric oxide releasing solution provides for extended nitric oxide production, thereby providing continuous delivery of therapeutic nitric oxide to the respiratory system of the subject.

The duration of administering the nitric oxide releasing solution to the subject may be varied in order to obtain a desired delivery. In one embodiment, the nitric oxide releasing solution is administered to the subject over a time period of less than 5 seconds. In another embodiment, the nitric oxide releasing solution is administered to the subject over a time period of about 5 seconds. In another embodiment, the nitric oxide releasing solution is administered to the subject over a time period of about 30 seconds. In another embodiment, the nitric oxide releasing solution is administered to the subject over a time period of about 1 minute. In another embodiment, the nitric oxide releasing solution is administered to the subject over a time period of about 2 minutes. In another embodiment, the nitric oxide releasing solution is administered to the subject over a time period of about 10 minutes. In another embodiment, the nitric oxide releasing solution is administered to the subject over a time period of about 30 minutes.

In one aspect, the principles disclosed herein provide for the treatment, prevention, or reduction of incidence of a respiratory disease or disorder in a subject. Exemplary respiratory diseases or disorders that can be treated include, but are not limited to BRDc, porcine respiratory disease complex (PRDc), and the like. In some cases, the respiratory disease or disorder may be caused by a bacterium (e.g., *M. haemolytica, H. somni*, mycobacteria), fungus, a virus (e.g., Infectious Bovine Rhinotracheitis (IBR), Bovine Parainfluenza-3 (PI-3), and Bovine Respiratory Syncytial Virus (BRSV)), a protozoan, a parasite, and/or an arthropod, including a bacterium that has developed resistance to one or more antibiotics. Treatment of a respiratory disease by way of the present disclosure comprises the delivery of a nitric oxide releasing solution into the upper respiratory tract of the subject to be treated. For example, in certain embodiments, the nitric oxide releasing solution may be sprayed, inhaled, or instilled into the respiratory tract of the subject. The nitric oxide releasing solution may be administered to the respiratory tract of the subject via the nasal cavity or oral cavity of the subject. In one embodiment, the nitric oxide releasing solution is sprayed into the upper respiratory tract of the subject. In one embodiment, the solution is administered to the subject intranasally. In one embodiment, the solution is administered to the sinuses. The nitric oxide releasing solution provides for extended nitric oxide production, thereby providing continuous delivery of therapeutic nitric oxide to the respiratory tract of the subject.

With reference to FIG. 1, illustrated is an animal intranasal administration system 100 in accordance with an example of the present disclosure. The system 100 can include an animal intranasal administration device 101 that can be used for administering a fluid (e.g., nitric oxide releasing solution) to a nostril 103 of an animal 104. The system 100 can also include a fluid source 102 to provide the fluid to the intranasal administration device 101. In one aspect, the fluid provided by the fluid source 102 and/or administered by the device 101 to the animal 104 can be in a liquid or gas state. In some embodiments, the liquid may be prepared to have a desired viscosity.

The intranasal administration device 101 can include a nasal passage nozzle 110 for each nostril configured to receive fluid from the fluid source 102 fluidly coupled to the nasal passage nozzles, such as via a fluid conduit 120. The intranasal administration device 101 can also include a biasing mechanism to bias the nasal passage nozzles toward a septum 105 of the animal 104, such that the device is secured in place about the septum during administration of the fluid into nasal passages of the animal. The biasing action of each nozzle toward the septum allows the nasal passage nozzles or other parts of the device to effectively pinch the septum as they are on opposite sides thereof. The device can then be held in place as it pinches the septum. The animal intranasal administration system 100 can also include a pump 121 operable to deliver fluid from the fluid source 102 to the nasal passage nozzles 110. The pump 121 can be a motorized pump powered by electricity and/or a hand-operated pump. Any pump that is sufficient to deliver NORS in a volume and at a velocity that provides effective NO treatment can be used. In one example, NORS can be delivered at a velocity sufficient to ensure delivery of NORS liquid to the pharyngeal tonsillar material in the upper airway. Other deliver parameters and characteristics, such as volume, delivery time and variation can be selected and controlled in order to achieve a specific result, such as placing a specific volume of NORS at a specific physical location within a subject can be used, for example a set volume can be delivered with varying pressure, or a set time with a fixed pressure can be used to achieve a desired volume.

In one example, a hand-operated pump (e.g., a trigger operated vacuum hand pump) can be coupled to the fluid conduit 120 "inline" to deliver the fluid to the device 101 without the use of electricity. In one aspect, the fluid source can be portable by a user while in use. In some embodiments, the system 100 can include one or more carrying straps 126 coupleable to the fluid source 102 (e.g., directly coupled or coupled via a backpack or other carrying case) to facilitate portability by the user. Thus, in certain embodiments, the system 100 can be portable and powered entirely by the user. In alternative embodiments, the fluid source can be substantially stationary and in some cases can be attached to a post or other fixture. This embodiment can be advantageous when treating a large number of subjects as it allows a large volume of nitric oxide releasing solution to be utilized (i.e. from a large container).

The system 100 can include one or more valves associated with the fluid source 102, fluid conduit 120, and/or the device 101 to control the flow of fluid to the nasal passage nozzles 110, such as to control a fluid dosage to the animal 104. For example, a valve 106 can be located at or near the fluid source 102 and a valve 107 can be located at or near the device 101, although a valve may be disposed in any suitable location. In one aspect, a valve can be associated with one or both of the nasal passage nozzles 110 to control the flow of fluid to a specific nozzle. Any other mechanism for metering out a specific volume or dose of nitric oxide releasing solution for administration to the subject can also be used, including simply the amount of time over which the solution is administered (i.e. administration period) in combination with flow rate, etc.

In some embodiments, the fluid source 102 can comprise inactivated nitric oxide releasing solution 123, an activation agent 124, activated nitric oxide releasing solution, and/or nitric oxide gas. The activation agent 124 can be configured to activate the inactivated nitric oxide releasing solution 123 upon mixing. In one aspect, the activation agent 124 can be maintained separate from the inactivated nitric oxide releasing solution 123. The activation agent 124 can be in any suitable form, such as a solid (e.g., a powder, a tablet, and a capsule), a liquid (e.g., a solution), a gas, etc. The fluid source 102 can also comprise one or more containers 122 or reservoirs for the inactivated nitric oxide releasing solution 123, the activation agent 124, activated nitric oxide releasing solution, and/or nitric oxide gas. In general, the activation agent 124 and the inactivated nitric oxide releasing solution 123 can be at least partially mixed in a mixing chamber 125, which can be within the container 122. Thus, in one aspect, the inactivated nitric oxide releasing solution 123 can be activated within the container 122 and dispensed or delivered to the device 101 to be administered to the animal 104. The pump 121 can convey activated nitric oxide releasing solution from the fluid source 102 to the device 101. Alternatively, activated nitric oxide releasing solution can be conveyed from the fluid source 102 to the device 101 by pressure in the container 122 due to the production of nitric oxide gas resulting from activation of the nitric oxide releasing solution. In other words, an increase in gas pressure in the container 122, due to the formation of nitric oxide, can cause activated nitric oxide releasing solution to move from the container 122 to the device 101 via the fluid conduit 120 for delivery to the animal. In such embodiments, pump 121 may not be needed, or can be utilized if the pressure inside the container 122, becomes insufficient to continue dispensing the nitric oxide releasing solution at the desired rate/volume. In an alternative embodiment as described more fully below, a pump, either electric or manually operated, can be used to create pressure within the container and facilitate administration of the nitric oxide releasing solution.

Figure 2A:
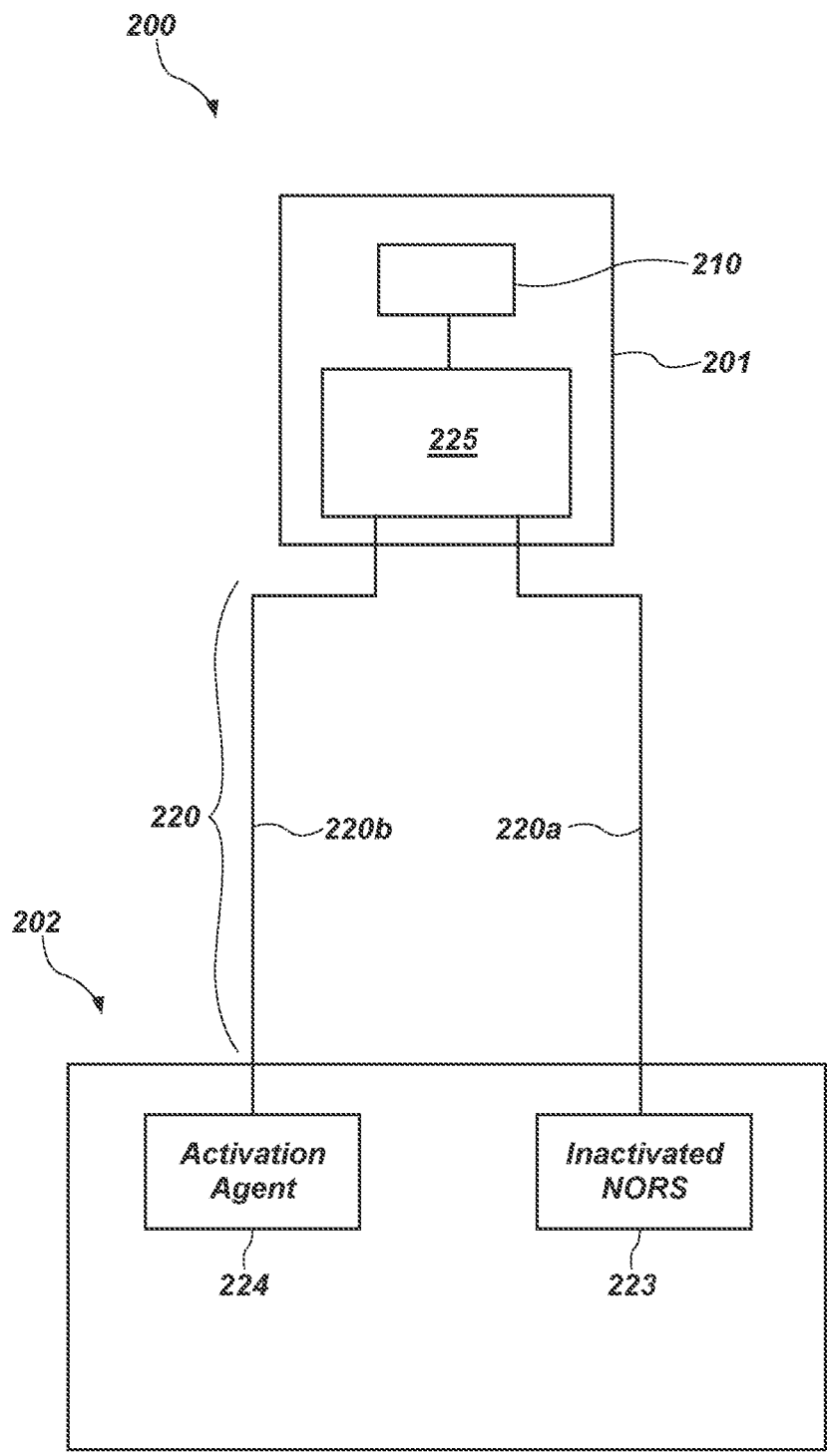
FIG. 2A is a schematic illustration of an animal intranasal administration system, in accordance with another example of the present disclosure.
Figure 2B:
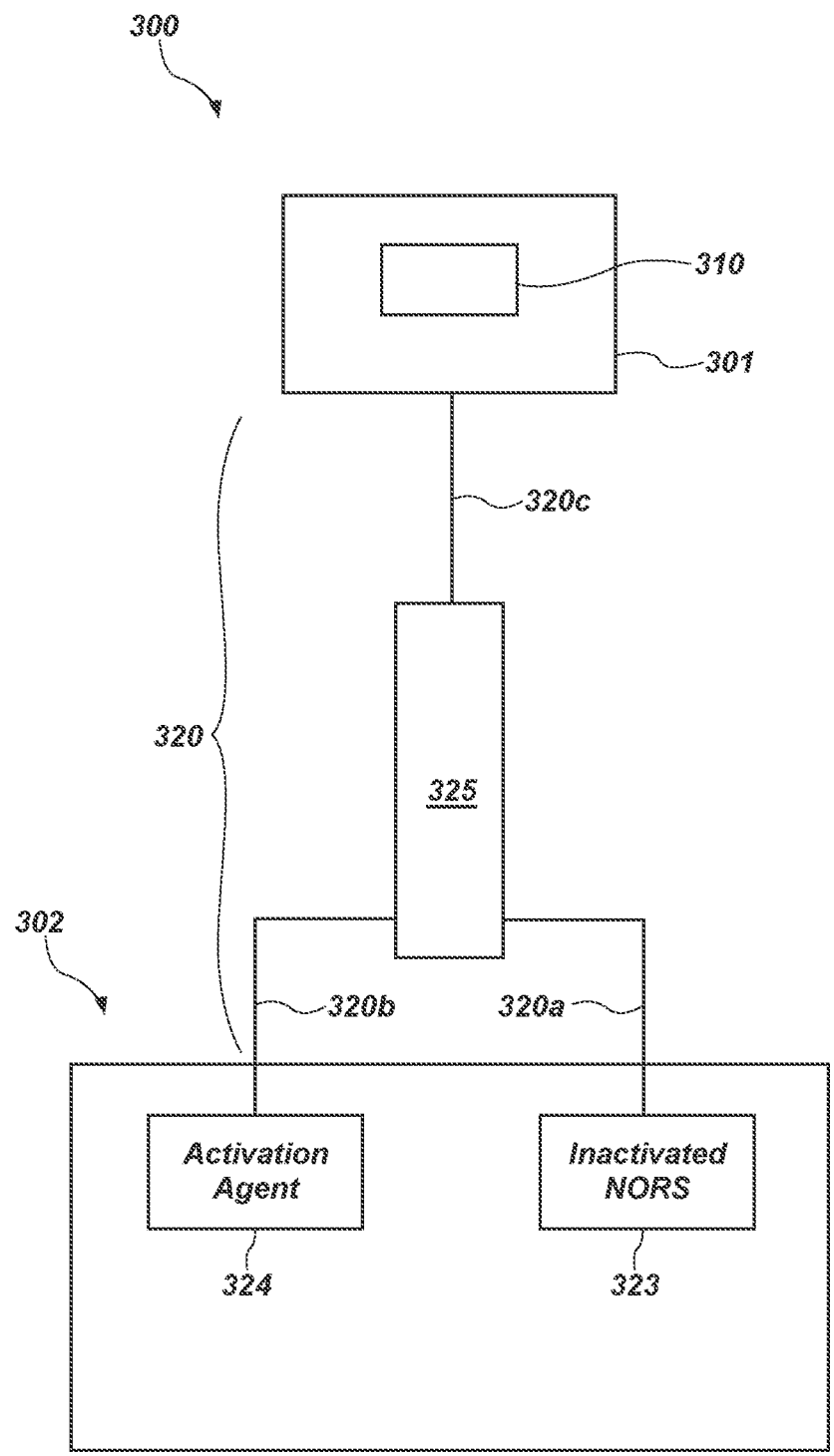
FIG. 2B is a schematic illustration of an animal intranasal administration system, in accordance with yet another example of the present disclosure.
Figure 2C:
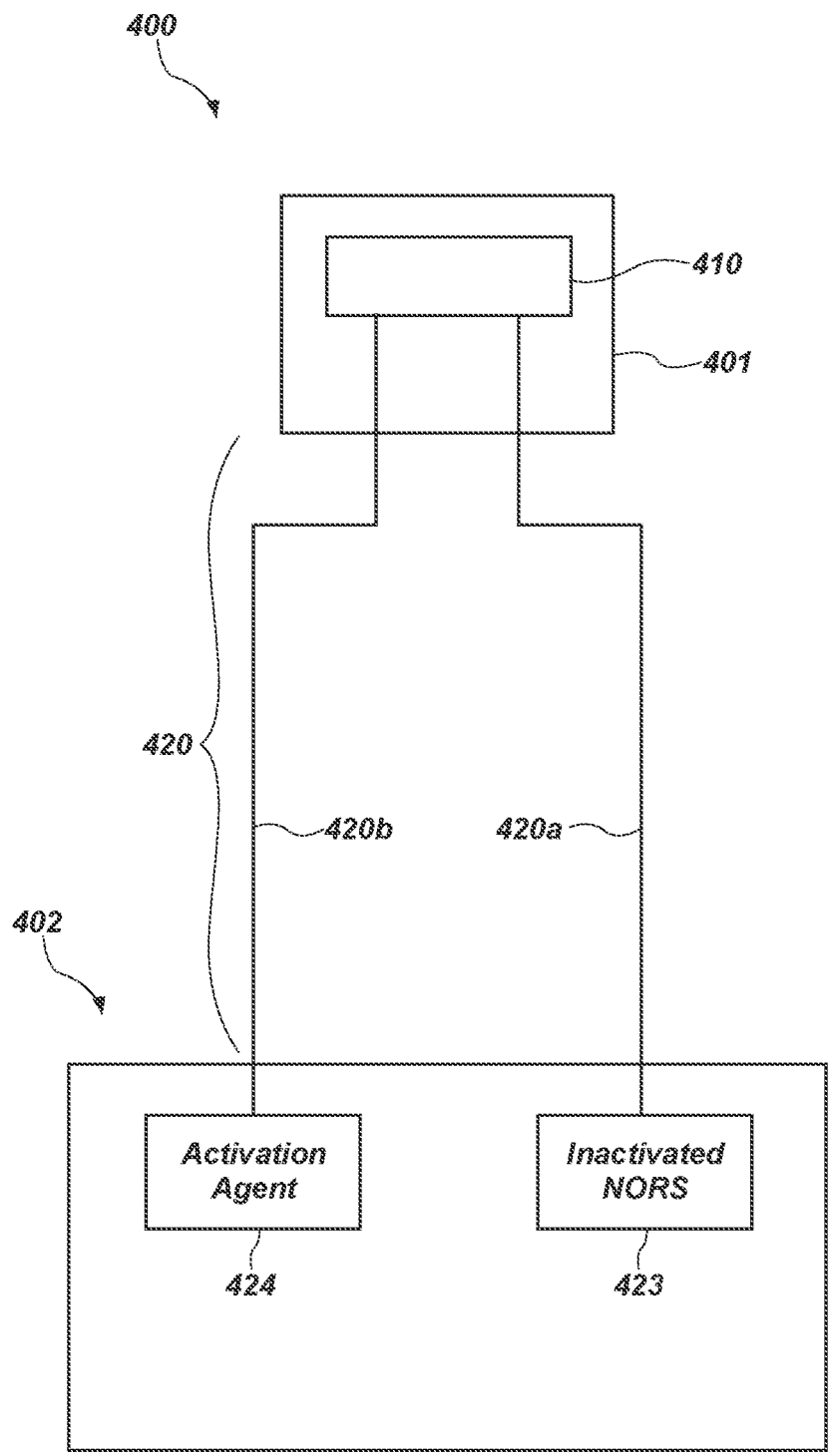
FIG. 2C is a schematic illustration of an animal intranasal administration system, in accordance with still another example of the present disclosure.

In another aspect, illustrated in FIGS. 2A-2C, an activation agent and inactivated nitric oxide releasing solution can be at least partially mixed in a mixing chamber external to a container, such as the container 122 of FIG. 1. For example, as shown in FIG. 2A, an intranasal administration system 200 can include a fluid source 202 fluidly coupled to an intranasal administration device 201 (e.g., to nasal passage nozzles 210) via a conduit 220, which includes a conduit 220a associated with inactivated nitric oxide releasing solution 223 and a conduit 220b associated with an activation agent 224, each of which can be disposed in separate containers. The conduits 220a, 220b can combine prior to the nasal passage nozzles 210, such as in a mixing chamber 225 within the intranasal administration device 201, such that mixing of the inactivated nitric oxide releasing solution 223 and the activation agent 224 occurs between the fluid source 202 and the nasal passage nozzles 210. Thus the nitric oxide releasing solution can be activated, or in other words, the activated solution can be formed, during delivery or administration of the nitric oxide releasing solution to a subject.

In another example, shown in FIG. 2B, an intranasal administration system 300 can include a fluid source 302 fluidly coupled to an intranasal administration device 301 (e.g., to nasal passage nozzles 310) via a conduit 320, which includes a conduit 320a associated with inactivated nitric oxide releasing solution 323 and a conduit 320b associated with an activation agent 324, each of which can be disposed in separate containers. The conduits 320a, 320b can combine prior to the nasal passage nozzles 310, such as in a mixing chamber 325 external to the fluid source 302 and the intranasal administration device 301, such that mixing of the inactivated nitric oxide releasing solution 323 and the activation agent 324 occurs between the fluid source 302 and the nasal passage nozzles 310. In one aspect, the mixing chamber 325 can comprise at least a portion of the conduit 320 such that mixing of the inactivated nitric oxide releasing solution 323 and the activation agent 324 takes place "in-line" to the intranasal administration device 301. Accordingly, the mixing chamber 325 can comprise any suitable structure, such as tubing, that can be disposed between the fluid source 302 and the intranasal administration device 301 and serve to mix the inactivated nitric oxide releasing solution 323 and the activation agent 324. The mixing chamber 325 can form an integral part of tubing that forms the conduit 320 or the mixing chamber 325 can be a separate component coupled to tubing to form a portion of the conduit 320. Activated nitric oxide releasing solution can be conveyed to the intranasal administration device 301 from the mixing chamber 325 via conduit 320c.

In yet another example, shown in FIG. 2C, an intranasal administration system 400 can include a fluid source 402 fluidly coupled to an intranasal administration device 401 (e.g., to nasal passage nozzles 410) via a conduit 420, which includes a conduit 420a associated with inactivated nitric oxide releasing solution 423 and a conduit 420b associated with activation agent 424, each of which can be disposed in separate containers. The conduits 420a, 420b can combine at the nasal passage nozzles 410, which can form a mixing chamber, such that mixing of the inactivated nitric oxide releasing solution 423 and the activation agent 424 occurs at the nasal passage nozzles 410. Accordingly, the nasal passage nozzles 410 can comprise any suitable structure that can serve to accommodate the introduction of solution from multiple conduits and mix the inactivated nitric oxide releasing solution 423 and the activation agent 424. Thus, the conduits 420a, 420b can remain separate from the fluid source 402 to the nasal passage nozzles 410 such that mixing of the inactivated nitric oxide releasing solution and the activation agent occurs at an animal engaged by the intranasal administration device 401. In other words, the nitric oxide releasing solution is activated or formed in-vivo at the administration site, or after being dispensed from the nozzle.

In one aspect, each nasal passage nozzle can receive either an activation solution or inactivated nitric oxide releasing solution, such that each is administered to the animal separately. Thus, the activation solution and the inactivated nitric oxide releasing solution can mix after being dispensed from the intranasal administration device at or inside the animal, such as inside a nasal passage, to activate the nitric oxide releasing solution. In some embodiments, each nozzle may have separate openings and supporting fluidic connections to the respective sources of activation agent and nitrite solution (i.e. inactivated NORS). In this way, solution from each source can be brought to the nozzle separately, yet simultaneously for delivery to a subject concurrently. A nozzle can have a single opening and the solutions can be alternately administered, for example, a spray of inactivated NORS (i.e. nitrite solution, citric acid) followed by a spray of activator solution (e.g. citric acid, ascorbic acid, nitrite solution, etc.).

Figure 3A:
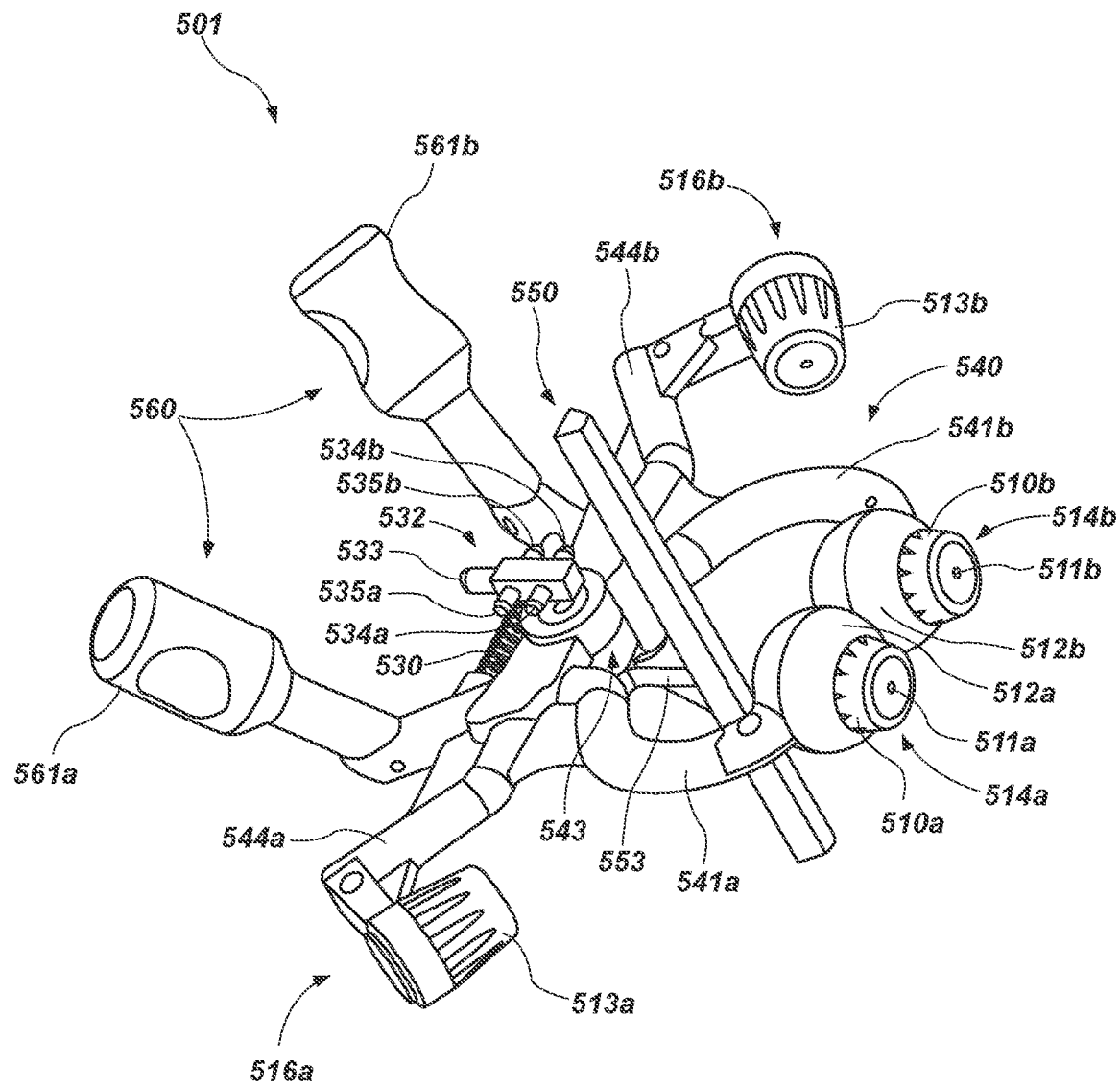
FIG. 3A is a perspective view of an animal intranasal administration device, in accordance with an example of the present disclosure.
Figure 3B:
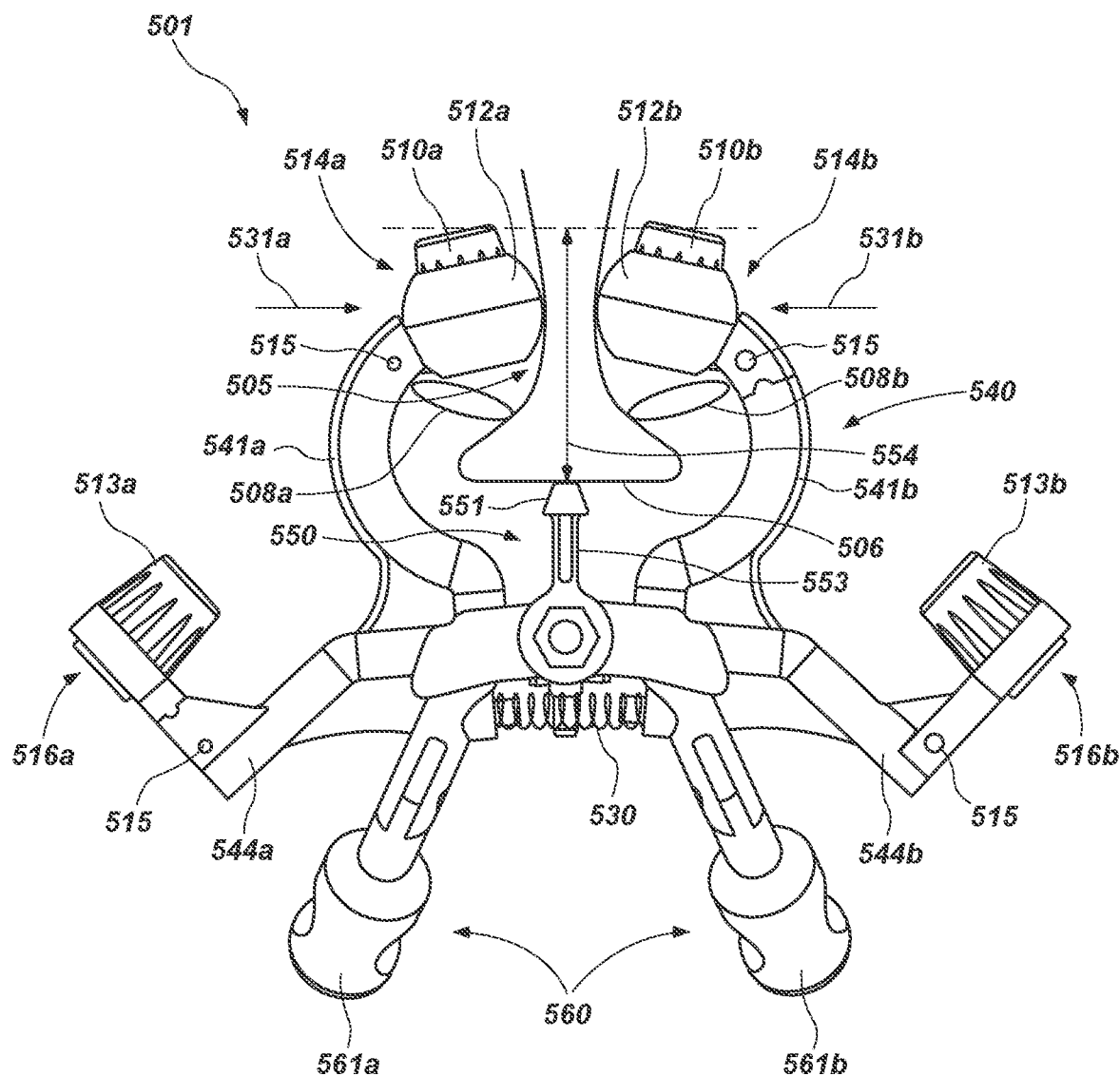
FIG. 3B is a bottom view of the animal intranasal administration device of FIG. 3A engaged with a septum of an animal.
Figure 3C:
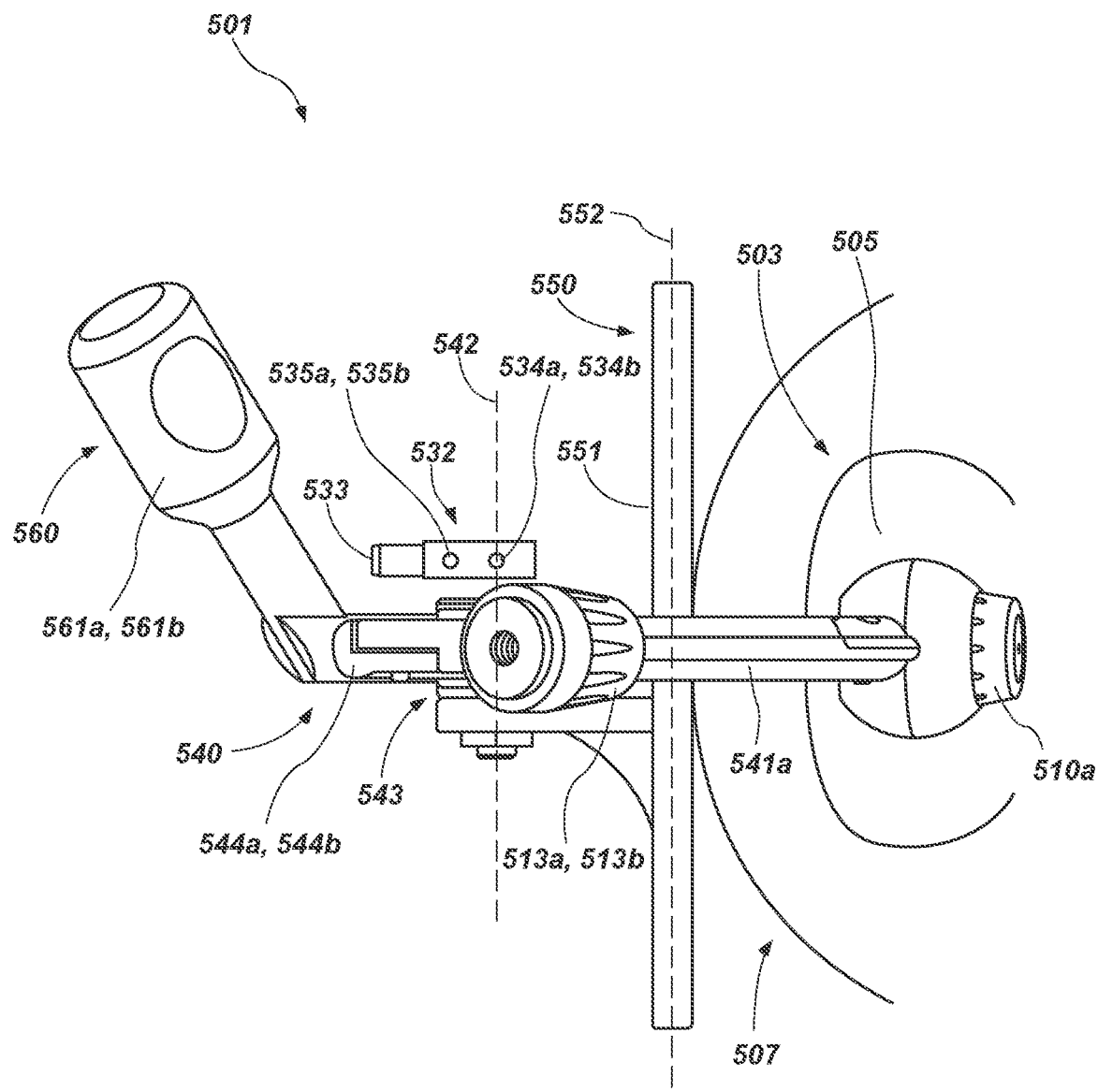
FIG. 3C is a side view of the animal intranasal administration device of FIG. 3A engaged with a septum of an animal.

FIGS. 3A-3C illustrate an animal intranasal administration device 501 in accordance with an example of the present disclosure. The intranasal administration device 501 can include a nasal passage nozzle 510a, 510b for each nostril 503 (FIG. 3C) configured to receive fluid from a fluid source, as described hereinabove. The intranasal administration device 501 can also include a biasing mechanism 530 to bias the nasal passage nozzles 510a, 510b toward a septum 505 (FIGS. 3B and 3C) of an animal, such that the device 501 is secured in place about the septum 505 during administration of the fluid into nasal passages of the animal.

In one aspect, the intranasal administration device 501 can include a support member 540 having support member portions 541a, 541b coupled to, and in support of, the nasal passage nozzles 510a, 510b, respectively. The support member portions 541a, 541b can be movable relative to one another (i.e., pivotally coupled to one another at pivot coupling 543) to secure the nasal passage nozzles 510a, 510b at least partially within the nostrils 503 of the animal about the septum 505 and such that fluid is directed into nasal passages of the animal. Thus, the nasal passage nozzles 510a, 510b can be oriented to align nozzle openings 511a, 511b with nasal passages when the device 501 is engaged with the septum 505 of the animal to provide for delivery of fluid to deep nasal passages.

In one aspect, the nasal passage nozzles 510a, 510b can be configured to direct fluid into the nasal passages past nasal folds 508a, 508b which may exist in the animal, as represented in FIG. 3B. For example, a bovine may have an alar fold, a basal fold, and a straight fold. Thus, the nasal passage nozzles 510a, 510b can be configured to direct fluid into the nasal passages past one or more of such folds to deliver the fluid to deep nasal passages. In one example, the nasal passage nozzles 510a, 510b can be configured to extend or penetrate into the nostrils beyond one or more nasal folds 508a, 508b, as illustrated in FIG. 3B to reach as far as the nasopharyngeal tonsillar material of the nasopharynx. In another example, the nasal passage nozzles 510a, 510b can be located and oriented to direct the fluid past one or more nasal folds without extending or penetrating into the nostrils beyond one or more of the nasal folds. In short, any configuration required to effectively administer nitric oxide releasing solution into the nasal passages, or any other desired or specified location in the respiratory tract of any subject in a manner sufficient to allow the subject to receive effective nitric oxide therapy, given the subject's specific anatomy, can be used.

In one aspect, the support member portions 541a, 541b can be movable relative to one another by the biasing mechanism 530 to bias the nasal passage nozzles 510a, 510b toward a secured position about the septum 50 in direction 531a, 531b. For example, the biasing mechanism 530 can comprise a spring acting on the support member portions 541a, 541b to bias the support member portions 541a, 541b toward the secured position about the septum 505. The biasing mechanism 530 can therefore cause the nasal passage nozzles 510a, 510b to pinch the septum 505 therebetween so that the nozzles 510a, 510b are held in place in the nostrils 503. While illustrated as a spring, it is to be understood that the biasing mechanism 530 can be any device, part, or mechanism that is sufficient to provide the desired biasing action. Moreover, the biasing mechanism 530 can be located anywhere on the device 501 that is adequate to provide the desired biasing action. In one aspect, biasing or spring strength can be adjustable as desired to secure the device 501 to the animal without causing undue pain to the animal. In one aspect, the support member 540 can be configured to provide clearance about a tip 506 of the septum 505. For example, the support member portions 541a, 541b can comprise arcuate configurations to provide clearance about the tip 506 of the septum 505, as illustrated in FIG. 3B.

The intranasal administration device 501 can include a septum interface portion 512a, 512b associated with the nasal passage nozzles 510a, 510b, respectively, to interface with the septum 505 and position the nasal passage nozzles to facilitate directing fluid deep into the nasal passages of the animal. For example, the septum interface portion 512a, 512b can serve to space or position the nasal passage nozzles 510a, 510b and openings 511a, 511b at a sufficient distance from the septum 505 to facilitate and maintain dispersal or spray pattern coverage into the nasal passages without interference from the septum 505.

The intranasal administration device 501 can also include a positioning member 550 configured to contact the tip 506 of the septum 505 to facilitate and maintain proper positioning and/or orientation of the nasal passage nozzles 510a, 510b within the nostrils 503 of the subject so that the nasal passage nozzles 510a, 510b direct fluid in a direction substantially aligned with the nasal passage openings of the animal. In this way, positioning member 550 may act as a depth stop for maintaining proper positioning and/or orientation of the nasal passage nozzles 510a, 510b within the nostrils 503 of the subject. For example, the positioning member 550 can be configured to position the nasal passage nozzles 510a, 510b such that the openings 511a, 511b are at a depth 554 from the tip 506 of the septum 505 to properly position the nasal passage nozzles 510a, 510b at a suitable distance relative to the nasal passage openings. In one aspect, the positioning member 550 can comprise an elongated portion 551 having a longitudinal axis 552 that is substantially parallel to an axis 542 of rotation for movement of the support member portions 541a, 541b relative to one another. For example, the positioning member 550 can have a "T" configuration where a base portion 553 supports the elongated portion 551. The base portion 553 can be coupled to the support member 540, such as to one or both of the support member portions 541a, 541b, at the pivot coupling 543 of the support member portions 541a, 541b. The elongated portion 551 can be configured to contact a muzzle 507 of the animal to prevent or minimize sagging or downward rotation of the device 501 during use, thereby facilitating proper alignment of the nasal passage nozzles 510a, 510b.

The intranasal administration device 501 can include a user interface 560 coupled to the support member 540 to facilitate movement of the support member portions 541a, 541b relative to one another by a user. For example, the user interface 560 can include user interface portions 561a, 561b, such as handles, coupled to the support member portions 541a, 541b, respectively, to facilitate movement of the nasal passage nozzles 510a, 510b by a user in a direction opposite the biasing direction 531a, 531b, such as by squeezing the user interface portions 561a, 561b toward one another.

In one aspect, the intranasal administration device 501 can include one or more nostril nozzles 513a, 513b configured to direct fluid onto the nostrils 503 of the subject. In a particular aspect, the nostril nozzles 513a, 513b can be configured to direct fluid onto the anterior nostrils. The nostril nozzles 513a, 513b can be coupled to the support member 540. For example, the support member 540 can comprise lateral extension portions 544a, 544b to position the nostril nozzles 513a, 513b, respectively. In one aspect, the lateral extension portions 544a, 544b can be coupled to, and extend from, the support member portions 541a, 541b, respectively. In another aspect, the intranasal administration device 501 can include one or more muzzle nozzles (not shown in these figures) configured to direct fluid onto the muzzle 507 of the animal. A muzzle nozzle can be supported by one or more of the support member portions 541a, 541b and/or the lateral extension portions 544a, 544b. As such, delivery of the nitric oxide releasing solution can be made to both the nasal passages and the nares simultaneously, or at the very least, using a single device.

Although the intranasal administration device 501 is shown with four total nozzles, it should be recognized that an intranasal administration device in accordance with the present disclosure can include any suitable number of nozzles, which can have an appropriate dispersal or spray pattern directed at an appropriate angle to any suitable area of an animal's muzzle, nares, nostrils, nasal passage, etc. In other words, nozzle dispersal or spray patterns can be specifically suited for a particular area (i.e., the nasal passages, nostrils, muzzle, etc.) and can be oriented at any suitable angle to direct fluid onto or into the area. In one aspect, one nozzle can be configured to direct fluid onto multiple areas. For example, the nostril nozzles 513a, 513b can be configured to disperse or spray fluid on the nares and the muzzle. Thus, the nozzles of an intranasal administration device in accordance with the present disclosure can be configured to have various dispersal or spray patterns to cover nasal passages and entry surfaces into the nasal passages. Nozzles used with the device 501 may therefore initiate any spray pattern known in the art suitable for a given purpose or dispersing target region.

In one aspect, the intranasal administration device 501 can include a fluid distribution manifold 532 fluidly coupled to the nozzles of the device 501. For clarity, external fluid couplings or conduits, such as tubing or hoses, have been omitted in FIGS. 3A-3C. The fluid distribution manifold 532 can have an inlet port 533 to receive fluid from a fluid source and outlet ports 534a, 534b, 535a, 535b to distribute fluid to the various nozzles of the device 501. For example, outlet ports 534a, 534b can be fluidly coupled to the nasal passage nozzles 510a, 510b, respectively, and outlet ports 535a, 535b can be fluidly coupled to the nostril nozzles 513a, 513b, respectively. Thus, each of the nasal passage nozzles 510a, 510b and the nostril nozzles 513a, 513b can be configured to couple with a conduit to receive fluid from a fluid source. Although the fluid distribution manifold 532 is shown separate from other structural components of the device 501, such as the support member 540 or the positioning member 550, it should be recognized that a fluid distribution manifold can be coupled to or integrally formed with any structural portion of the device 501, such as one or more portions of the support member 540 and/or the positioning member 550. In one aspect, the fluid manifold 532 can include at least two inlet ports and a mixing chamber, as discussed above, such that mixing of inactivated nitric oxide releasing solution and activation agent occurs between a fluid source and the nasal passage nozzles 510a, 510b. In another aspect, the fluid distribution manifold 532 can include one or more valves to control fluid flow one or more nozzles of the device 501.

In one aspect, the support member 540 can have internal fluid conduits defined by one or more openings or passageways through the support member 540. For example, one or more of the support member portions 541a, 541b can include at least a portion of a fluid conduit to direct fluid to the respective nasal passage nozzle 510a, 510b from the fluid source. Similarly, one or more of the lateral extension portions 544a, 544b can include at least a portion of a fluid conduit to direct fluid to the respective nostril nozzle 513a, 513b from the fluid source. Thus, such internal fluid conduits can receive fluid directly from the fluid source or after distribution from the fluid distribution manifold 532.

In one aspect, the intranasal administration device 501 can be constructed to facilitate interchangeability of parts. For example, the support member portions 541a, 541b can be configured to removably couple with nozzle or spray heads 514a, 514b, such as with fasteners 515. Similarly, the lateral extension portions 544a, 544b can be configured to removably couple with nozzle or spray heads 516a, 516b, such as with fasteners 515. In addition, the support member portions 541a, 541b can be configured to removably couple with the user interface portions 561a, 561b. Furthermore, the biasing member or spring 530 can be removably coupled to the support member 540. Thus, nozzles, springs, handles, positioning members, etc. can be interchangeable and replaced as desired to accommodate different animal species and/or animals of a different size. Thus, the device 501 can be configured and customized for the anatomy of a cow of a given age. In one aspect, the intranasal administration device 501 can be disassembled to facilitate cleaning and/or servicing of the various parts or components of the device.

In one aspect, the nozzle or spray heads 514a, 514b can include or incorporate the nasal passage nozzles 510a, 510b as well and the septum interface portions 512a, 512b, respectively. As illustrated in FIGS. 3A-3C, the spray heads 514a, 514b can have a spherical or ball configuration that provides a curved interface surface for the septum interface portions 512a, 512b for contacting the septum 505. Such a spherically curved surface can accommodate various septum thicknesses and maintain a consistent interface with the septum 505. The spherical surface can have a diameter configured to provide adequate surface area for effective "clamping" (i.e. pinching) contact with the septum without providing excessive pressure to the contact area of the septum such that the device 501 is uncomfortable for the animal. The diameter of the spherical surface can also contribute to providing adequate space for the nasal passage nozzles 510a, 510b from the septum to provide and maintain a suitable dispersal or spray pattern.

Figure 4:
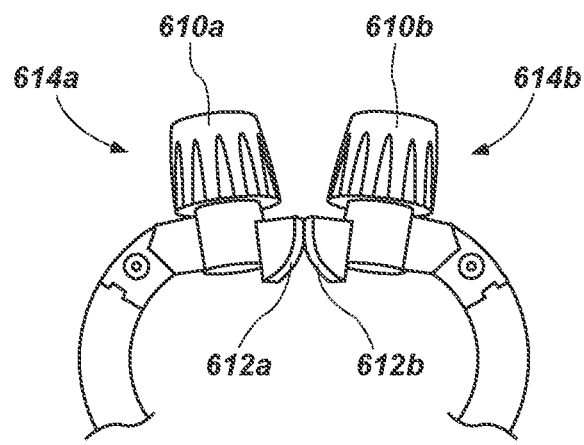
FIG. 4 is an isolated view of animal intranasal administration device spray heads, in accordance with an example of the present disclosure.

FIG. 4 illustrates nozzle or spray heads 614a, 614b in accordance with another example of the present disclosure. As with the spray heads 514a, 514b of FIGS. 3A-3C discussed above, the spray heads 614a, 614b can include or incorporate nasal passage nozzles 610a, 610b as well as septum interface portions 612a, 612b, respectively. In this case, the spray heads 614a, 614b have a fan configuration with an arcuate surface for the septum interface portions 612a, 612b for contacting a septum. Such an arcuate curved surface can accommodate various septum thicknesses and may be useful when a higher contact pressure is desired, due to the relatively small contact area that can be provided by this configuration. The size of the arcuate surface can also contribute to providing adequate space for the nasal passage nozzles 610a, 610b from a septum to provide and maintain a suitable dispersal or spray pattern.

Figure 5:
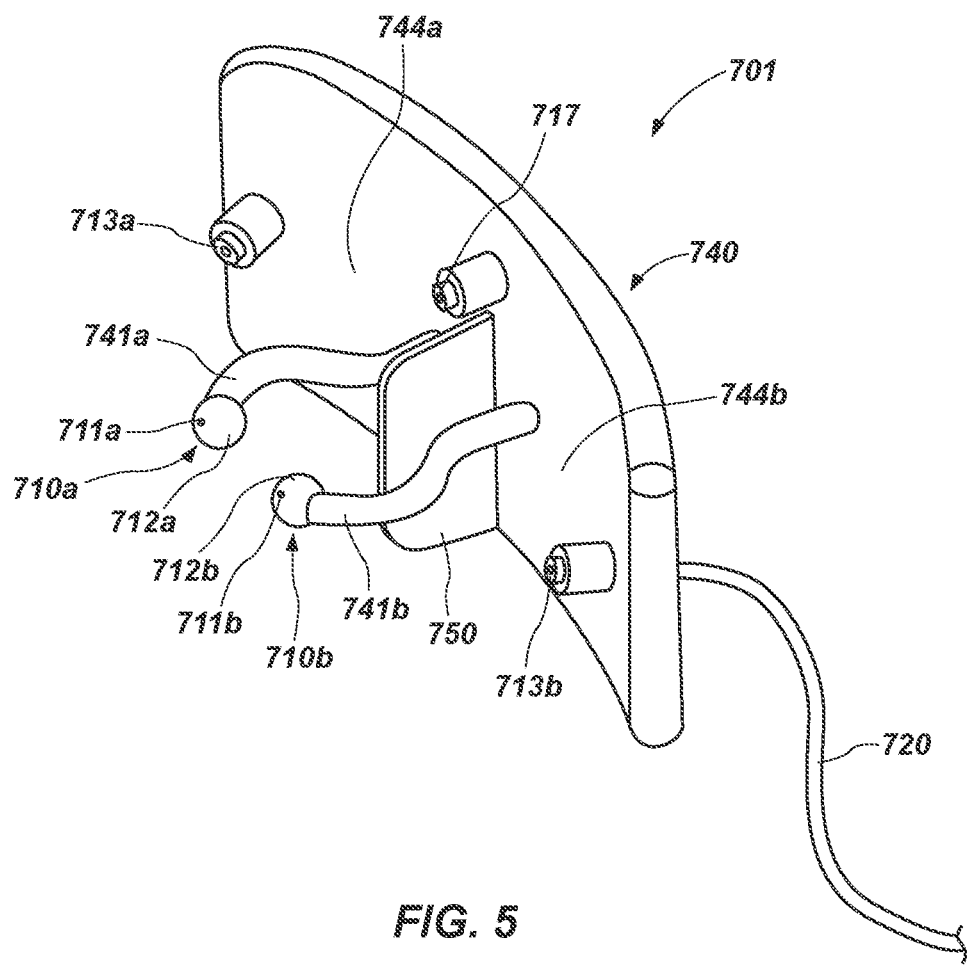
FIG. 5 is a perspective view of an animal intranasal administration device, in accordance with another example of the present disclosure.
Figure 7:
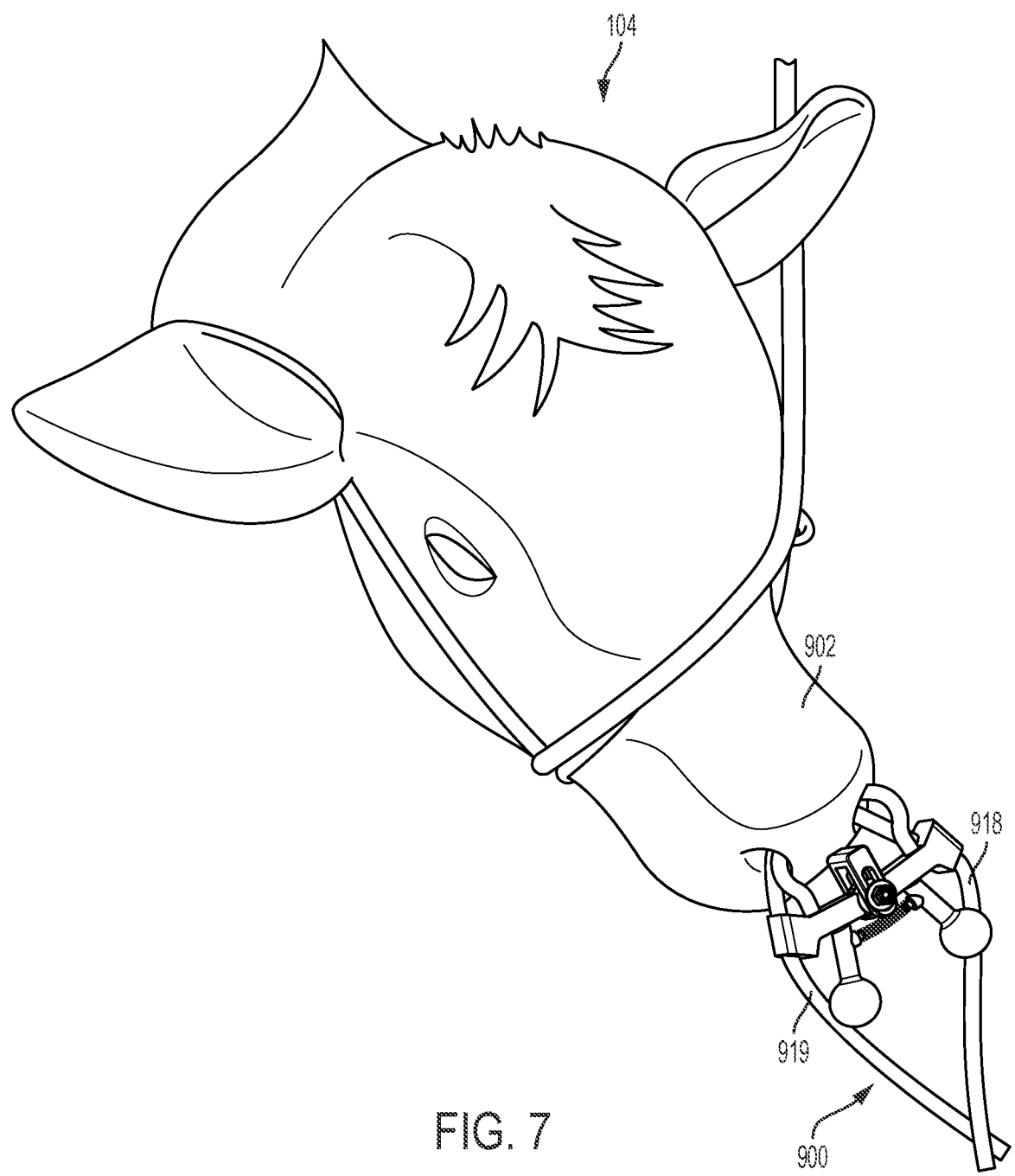
FIG. 7 is a perspective view of the head of an animal showing an intranasal administration device coupled to the nose of the animal, in accordance with another example of the present disclosure.
Figure 8:
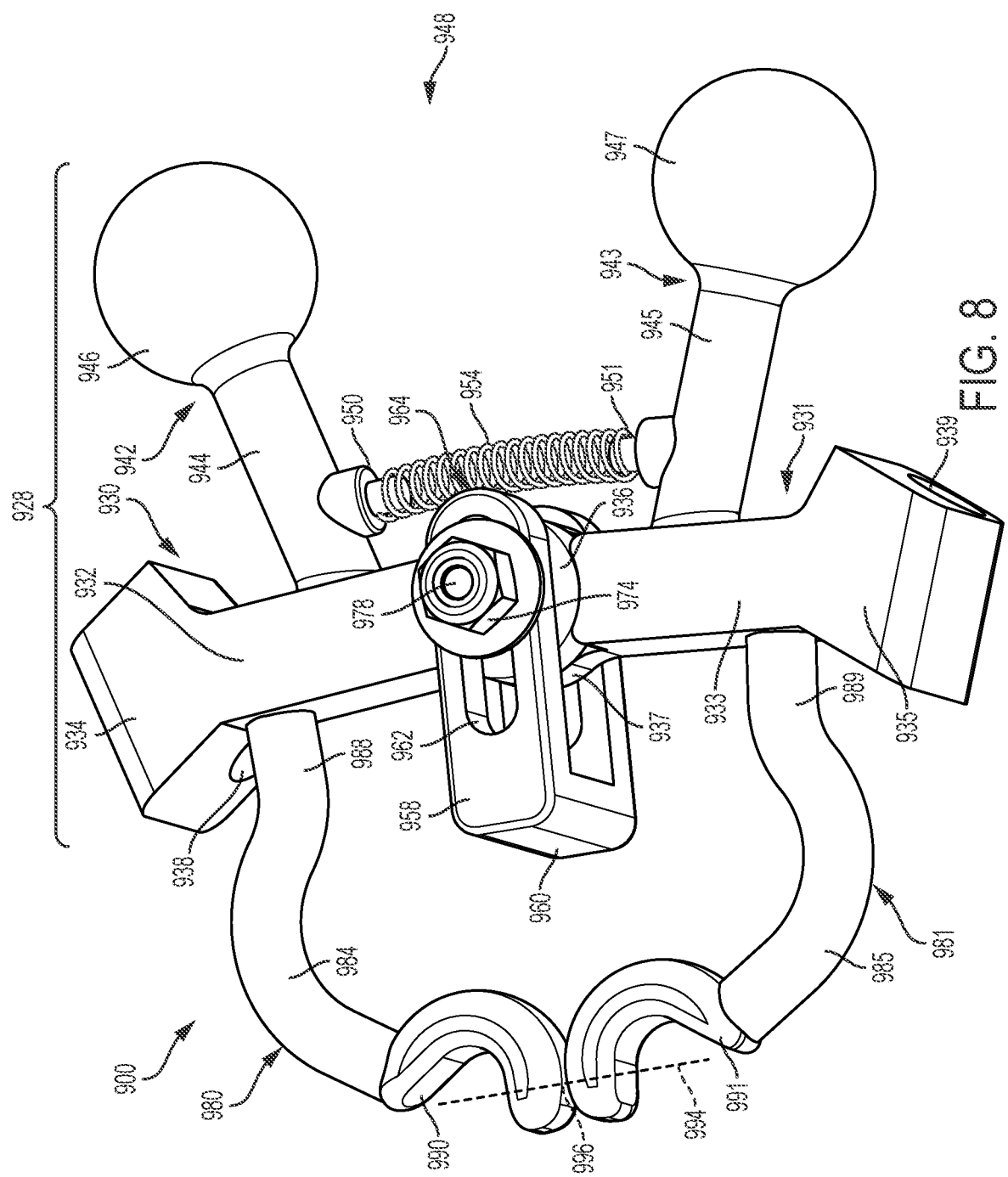
FIGS. 8 and 9 are perspective and top views of the intranasal administration device depicted in FIG. 7.

FIG. 5 illustrates an animal intranasal administration device 701 in accordance with another example of the present disclosure. The intranasal administration device 701 can include a nasal passage nozzle 710a, 710b for each nostril configured to receive fluid from a fluid source, as described hereinabove. In one aspect, the intranasal administration device 701 can include a support member 740 having support member portions 741a, 741b coupled to, and in support of, the nasal passage nozzles 710a, 710b, respectively. In one aspect, the support member 740 can be resiliently flexible or include resiliently flexible components. Thus, in a particular aspect, one or both of the support member portions 741a, 741b can be resiliently flexible and therefore movable relative to one another to secure the nasal passage nozzles 710a, 710b at least partially within the nostrils of an animal about a septum and such that fluid is directed into nasal passages of the animal. The resilient flexibility of the support member portions 741a, 741b can provide a biasing mechanism to bias the nozzles 710a, 710b toward a septum of an animal, such that the device 701 is secured in place about the septum during administration of the fluid into nasal passages of the animal. Thus, the resilient flexibility of the support member portions 741a, 741b can bias the nasal passage nozzles 710a, 710b toward a secured position about the septum 70 in direction 731a, 731b. The nasal passage nozzles 710a, 710b can be oriented to align nozzle openings 711a, 711b with nasal passages when the device 701 is engaged with the septum of the animal to provide for delivery of fluid to deep nasal passages.

The intranasal administration device 701 can also include a septum interface portion 712a, 712b associated with the nasal passage nozzles 710a, 710b, respectively, to interface with the septum and position the nasal passage nozzles to facilitate directing fluid deep into the nasal passages of the animal. For example, the septum interface portion 712a, 712b can serve to space or position the nasal passage nozzles 710a, 710b and openings 711a, 711b away from the septum to facilitate and maintain dispersal or spray pattern coverage into the nasal passages without interference from the septum. The septum interface portions 712a, 712b are illustrated with a spherical configuration, although any suitable configuration may be utilized.

The intranasal administration device 701 can further include a positioning member 750 configured to contact a tip of the septum to facilitate and maintain proper positioning and/or orientation of the nasal passage nozzles 710a, 710b within the nostrils of the animal so that the nasal passage nozzles 710a, 710b direct fluid in a direction substantially aligned with the nasal passage openings of the animal. For example, the positioning member 750 can be configured to position the nasal passage nozzles 710a, 710b such that the openings 711a, 711b are at a distance from the tip of the septum to properly position the nasal passage nozzles 710a, 710b at a suitable distance relative to the nasal passage openings. In one aspect, the positioning member 750 can be coupled to the support member 740, such as between the support member portions 741a, 741b. The positioning member 750 can be configured to contact a muzzle of the animal when the device 701 is engaged with the animal to prevent or minimize sagging or downward rotation of the device 701 during use, thereby facilitating proper alignment of the nasal passage nozzles 710a, 710b.

In one aspect, the intranasal administration device 701 can include one or more nostril nozzles 713a, 713b configured to direct fluid onto the nostrils of the animal. In particular, the nostril nozzles 713a, 713b can be configured to direct fluid onto the anterior nostrils. In one aspect, the nostril nozzles 713a, 713b can be coupled to the support member 740. For example, the support member 740 can comprise lateral extension portions 744a, 744b to position the nostril nozzles 713a, 713b, respectively. In another aspect, the intranasal administration device 701 can include one or more muzzle nozzles 717 configured to direct fluid onto a muzzle of the animal. The muzzle nozzle 717 can be coupled to the support member 740 at any suitable location.

FIGS. 6A-6C illustrate aspects of an animal intranasal administration system 800 in accordance with another example of the present disclosure. The system 800 can include an animal intranasal administration device 801 of any suitable configuration described hereinabove for administering a fluid to a nostril of an animal. The system 800 can also include a fluid source 802 to provide the fluid to the intranasal administration device 801, such as via a fluid conduit 820. The fluid source 802 can comprise inactivated nitric oxide releasing solution, an activation agent, activated nitric oxide releasing solution, and/or nitric oxide gas.

In one aspect, the fluid source 802 can comprise a container 822 or a reservoir with inactivated nitric oxide releasing solution disposed therein. The container 822 may be of any desired size and shape. In one aspect, the container 822 can be suitable for holding multiple doses or application volumes of nitric oxide releasing solution without requiring a refill. The fluid source 802 can also have a fluid outlet port 870, which can be configured to couple with the fluid conduit 820 for delivering the fluid to the device 801. The fluid outlet port 870 can be associated with a cap 871 (as shown) or with the container 822. A sump conduit 872 can be fluidly coupled to the fluid outlet port 870 to deliver fluid to the fluid outlet port 870. The sump conduit 872 will typically extend to a bottom of the container 822 to facilitate evacuating substantially all the fluid from the container 822. The sump conduit 872 can be associated with the cap 871 (as shown) and/or with the container 822 (e.g., molded into a side of the container 822). The fluid source 802 can also include a gas port 873 to allow a gas into the container 822 during use of the system 800. For example, a pump 821 can be a gas pump and can be fluidly coupled to the gas port 873 by a conduit to provide pressurized gas (e.g., air or other suitable gas) to the container 822 such that "head space pressure" in the container 822 causes the fluid to exit the container 822 via the sump conduit 872 and fluid outlet port 870 for delivery to the device 801 through the fluid conduit 820. The gas port 873 can be associated with the cap 871 (as shown) or with the container 822. The gas port 873 will typically be located above a level of the inactivated nitric oxide releasing solution in the container 822. In one aspect, the container 822 can be pressurized to about 50 psig during operation (with about 30 psig being typical), although the system can be configured to operate at any suitable pressure. In one aspect, the pump 821 can provide a pressure to deliver a specific spray volume onto the muzzle and into the nares and nasal passages of an animal. In one aspect, a pressure gage or sensor (i.e., as part of the pump 821) can monitor pressure in the container 822 and/or the fluid conduit 820 to determine whether a nozzle has been clogged.

In one aspect, the pump 821 can be a liquid pump and can operate to pump liquid fluid out of the container 822 without creating head space pressure in the container 822. The pump 821 can be a gas pump and/or a liquid pump of any suitable configuration. In one aspect, the pump 821 can be a motorized pump powered by electricity and/or a hand-operated pump. A cover 874 can be provided for the cap 871 to protect the fluid outlet port 870 and the gas port 873 when not in use. Components of the system can be constructed with metals, plastics, and other polymers compatible with the activation agent (e.g., citric acid, sodium nitrite), nitric oxide releasing solution, and nitric oxide.

In one aspect, the fluid source 802 can include an activation agent maintained separate from the inactivated nitric oxide releasing solution. The activation agent can be configured to activate the inactivated nitric oxide releasing solution upon mixing. Once mixed, the production of nitric oxide in the solution can create a head space pressure sufficient to deliver fluid from the container 822 to the device 801. Thus, fluid can dispense automatically from the device 801 upon mixing the activation agent and the inactivated nitric oxide releasing solution utilizing a gas pressure resulting from the activation of the nitric oxide releasing solution.

The activation agent can be in any suitable form, such as a solid (e.g., a powder, a tablet, a capsule, etc.), a liquid (e.g., a solution), a gas, etc. In one aspect, an activation agent in solid form can be in a dissolvable pouch and/or supported by a cage 875, which can be configured to be disposed within the container 822 below the level of the inactivated nitric oxide releasing solution to ensure contact or mixing with the inactivated nitric oxide releasing solution. The cage 875 can include one or more openings to facilitate mixing of the activation agent and the inactivated nitric oxide releasing solution. Thus, when the activation agent is submerged in the inactivated nitric oxide releasing solution the activation agent will dissolve producing nitric oxide in the solution. The cage 875 can be coupled to the sump conduit 872 (as shown) and supported within the container above a bottom of the container 822 or simply dropped into the container 822. In one aspect, the cage 875 can be coupled to a rod or tube having an end that is located proximate an opening of the container 822. Coupling the cage 875 to the sump conduit 872 or a rod or tube can simplify retrieval of the cage 875.

In one aspect, the animal intranasal administration system 800 can be provided as a kit. For example, the container 822 can have a device coupling feature 880 to couple with and support the device 801. The container 822 can also have a handle 881. The handle 881 can have a free end 826 that can couple to a body of the container 822 via coupling features 882, 883. The coupling features 882, 883 can be configured to further capture and secure the device 801 to the container 822. A fluid conduit coupling feature 884 can extend from the free end 826 of the handle 881 to capture and secure the fluid conduit 820 to the container 822. In addition, the pump 821 can be configured to removably couple with a bottom of the container 822. If the pump 821 includes electrical components, a battery pack may be included. The cover 874 can cover the cap 871 and/or an opening of the container 822 when not in use.

In use of the system 800, an animal can arrive in a holding chute and a user can engage the intranasal administration device 801 with the animal's nostril, as described hereinabove or further below. Because the device 801 is secured to the animal, the user can administer fluid to the animal "hands free." The fluid source 802 can be supported by a post of the holding chute and can hold a volume (e.g., 5 gallons) of premixed nitric oxide releasing solution in its dormant state. Once the activation agent and the inactive nitric oxide releasing solution are mixed, nitric oxide gas is produced in the solution in the container 822. The activated nitric oxide releasing solution is then conveyed from the fluid source to the device 801 and dispensed or sprayed onto the treatment site or area, such as into the animal's nasal passages. For example, the activated solution may be sprayed into the nasal passages of the cattle in brief, measured bursts. In one aspect, the animal can receive one spray of about 8 mL into each nasal passage, twice, for a total of about 32 mL before being released. The duration of treatment administration can be between about 3-5 seconds. At the user's convenience the device 801 can be released or disengaged from the animal. The activated solution now lining the nasal passages of the animal can continue to release nitric oxide gas for up to 30 minutes or longer.

Furthermore, animal intranasal administration systems 100, 800 may be used in conjunction with any intranasal administration device according with the invention. Additional examples of intranasal administration devices are described below with reference to FIGS. 7 to 16. Generally, embodiments of the intranasal administration devices described below comprise fluid conduits including at the distal ends thereof nasal passage nozzles. The distal ends of the fluid conduits are detached from the septum interface portions, such that as the first and second support member portions, or jaws, are closed the nasal passage nozzles can move relative to the jaws. Movement may be laterally and/or in the anterior/posterior direction. The nasal passage nozzles may move to align with, and enter into, the ventral meatus. As used herein, the terms "open" and "close" mean, respectively, to separate the jaws or to bring them closer together. Thus, the jaws are opened to enable insertion thereof into the nostrils and are closed to clamp the nasal septum of the animal. The fluid conduits are secured to the intranasal administration device such that the angle formed by the centerlines of the fluid conduits at their distal ends is smaller when the jaws are open and increases as the jaws close.

In some embodiments, the fluid conduits are formed of a flexible material. The fluid conduits have lengths between their distal ends and areas where the fluid conduits are supported by the intranasal administration device which are sufficient to allow the flexible fluid conduits to bend due to contact with the tissue of the veterinary subject as the jaws are closed. Example flexible materials include PVC and vinyl. The combination of the self-alignment of the fluid conduits to the nasal septum and/or the ventral meatus and the insertion depth of the nasal passage nozzles into the nostrils enhances delivery of the fluid into the nasopharynx. In some instances it is desirable to substantially coat the nasal turbinates, the pharyngeal tonsillar material, and the nasopharynx of the animal. As used herein, the nasopharynx is substantially coated when at least 50% of its surface is coated by the fluid. Of course, to the extent possible the nasopharynx should be substantially coated without disturbing or causing trauma to the animal. In some embodiments, the jaws are sized and configured to minimally impede breathing of the animal during the intervention, and the jaws are blunted to reduce the likelihood of tissue damage. The distal ends of the jaws may comprise septum interference members which are twice as wide as they are thick, to enable clamping while permitting substantially unimpeded breathing by the animal.

Referring now to FIGS. 7 to 17, FIG. 7 is a perspective view of the head of an animal 104 with an intranasal administration device 900 including two fluid conduits 918, 919 extending into the nostrils of its nose 902. An intervention is performed by administering a fluid through at least one of fluid conduits 918, 919 into the nasopharynx 1164 of animal 104. An example intervention comprises delivery of nitric oxide, in various embodiments and variations thereof described hereinabove, including liquid, gas, gas releasing solution, and combinations thereof, to the nasopharynx to prevent, control, and/or treat bovine respiratory disease in bovine animals. Although the present invention may be described with reference to a particular animal species and disease, the invention is suitable to effect any other treatments intranasally with subjects of any other animal species.

Figure 17:
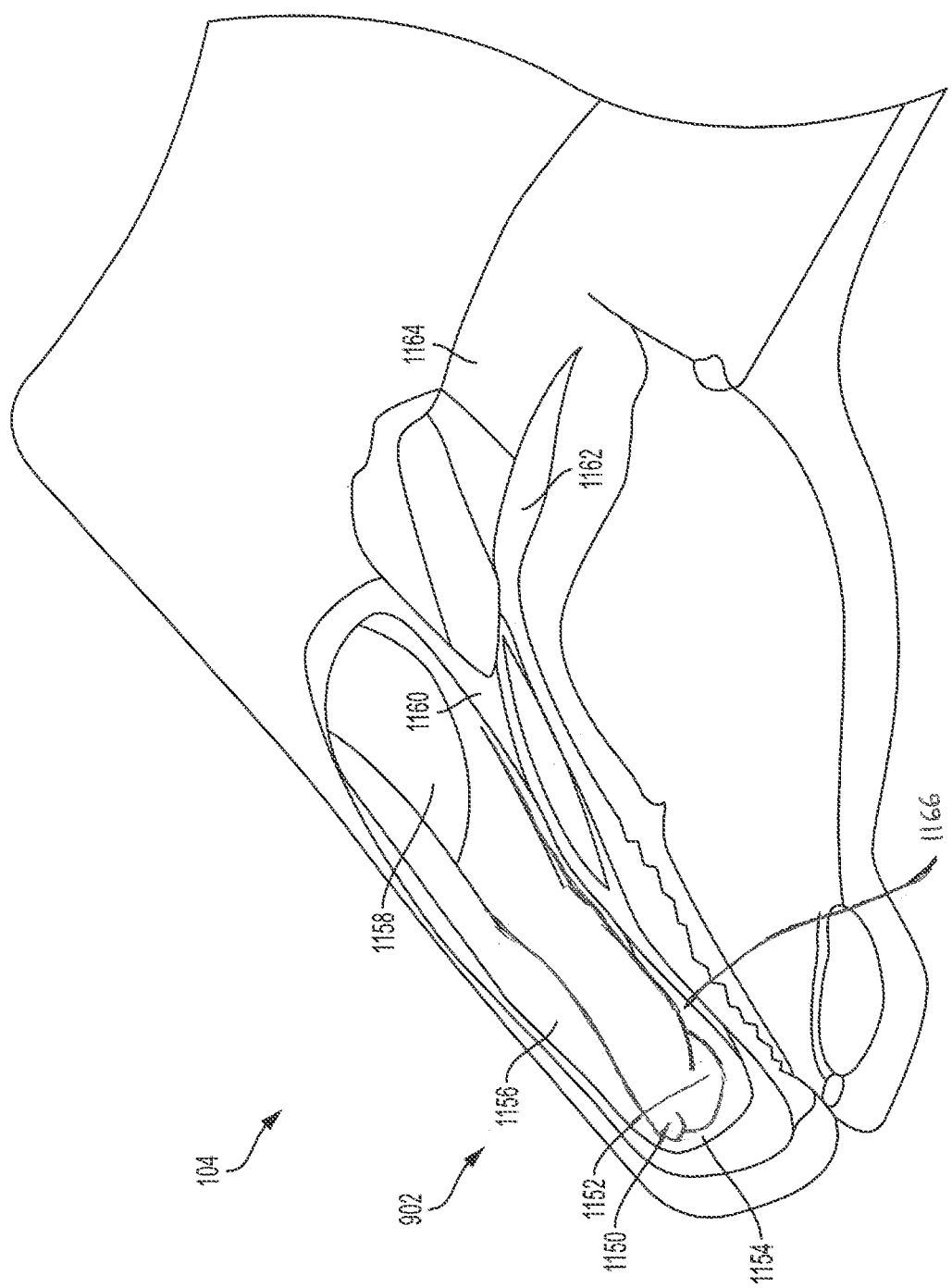
FIG. 17 is a schematic illustration of a sectioned head of a bovine animal.

A schematic illustration of a sectioned head of a bovine animal is depicted in FIG. 17 illustrating the alar fold 1150 and the basal fold 1152 at the nose of animal 104. The folds form a nasal constriction at the nasal vestibule 1154 which inhibits passage into the ventral meatus 1166 of the nasal passage. FIG. 17 further illustrates the locations of the dorsal nasal concha 1156, the middle nasal concha 1158, the nasal septum 1160, and the soft palate 1162 of the bovine animal. Intranasal administration devices in accordance with the disclosure include fluid conduits, e.g. tubes, which extend through the nasal constriction into ventral meatus 1166 of the nasal passage to facilitate discharge of fluid along a direction parallel to nasal septum 1160, which enables the fluid to reach nasopharynx 1164. Intranasal administration devices 900, 1000 are structured such that fluid conduits 918, 919 and nasal passage nozzles 920, 921 are inserted medially and posteriorly into ventral meatus 1166 to effectively reach into the cavities of interest.

Referring now to FIGS. 8 to 12, intranasal administration device 900 comprises fluid conduits 918, 919, nasal passage nozzles 920, 921 (best shown in FIGS. 10 and 11) inserted at the distal ends of fluid conduits 918, 919, an actuation mechanism 928, and first and second support member portions, or jaws, 980, 981. Actuation mechanism 928 comprises a first member 930 pivotally coupled by a joint mechanism 964 to a second member 931. Jaws 980, 981 extend distally from first and second members 930, 931, respectively. First member 930 comprises a first arm 932 having an opening at one end thereof (not shown) and a protrusion 934 at the opposite end. Protrusion 934 includes an elongate fluid conduit support opening 938 through which fluid conduit 918 passes. The portion of fluid conduit 918 in contact with elongate fluid conduit support opening 938 may be referred to as the "supported portion" of fluid conduit 918, which is opposite its distal end, in which nasal passage nozzles 920 is positioned. The distal end is thus unsupported and movable relative to the septum interface portion. The distance between the supported portion of the fluid conduit, and the flexibility of the fluid conduit, affect the amount of potential movement of the distal end relative to the distal ends of the septum interface portions. In some embodiments, a distance of about 2 or more inches provides sufficient flexibility. In some embodiments, a distance of about 3 or more inches provides sufficient flexibility. The force to cause such movement of the distal end is a result of insertion into the nasal passage and contact with the nasal septum during the insertion, thus the amount of force should be sufficiently small to avoid distressing the animal.

A first handle member 942 extends from first arm 932 and includes a first handle portion 944 and a second handle portion 946. Second member 931 comprises a second arm 933 having an opening at one end thereof (not shown) and a protrusion 935 at the opposite end. Protrusion 935 includes an elongate fluid conduit support opening 939 through which fluid conduit 919 passes. A second handle member 943 extends from second arm 933 and includes a first handle portion 945 and a second handle portion 947. First and second handle members 942, 943 form a handle 948, also referred to as a user interface. In use, the user compresses handle 948 against the tension provided by a biasing mechanism 954 to cause jaws 980, 981 to open, thereby allowing their insertion into the nostrils of the animal, and upon release of the compressive force by the user biasing mechanism 954 causes jaws 980, 981 to close, clamping nasal septum 1160. First handle portions 944, 945 are provided to extend second handle portions 946, 947 proximally from the pivot point of joint mechanism 964 to enhance actuation leverage. Second handle portions 946, 947 have larger contact surfaces than first handle portions 944, 945 to increase the user's comfort when compressing them to open jaws 980, 981. Second handle portions 946, 947 may have spherical contact surfaces, may comprise spherical shapes, and may further comprise any shape with curves radiused to correspond to the fingers of the user to distribute the force applied by the user. Alternatively, or additionally, second handle portions 946, 947 may have elongated shapes to distribute the force along their length.

An angle 929 (shown in FIG. 9) formed by the centerlines 940, 941 of elongate fluid conduit support openings 938, 939 is larger when jaws 980, 981 are closed than when they are open. First and second securement members 950, 951 are provided in first handle portions 944, 945 to secure biasing mechanism 954. An example biasing mechanism 954 comprises a spring, as shown. Arms 932, 933 have decreased thickness portions 936, 937 at their ends and openings (not shown) in decreased thickness portions 936, 937 through which a bolt 978 passes. Bolt 978 is secured by a nut 974. Joint mechanism 964 is formed by decreased thickness portions 936, 937, nut 974, and bolt 978.

In the present embodiment, a depth adjuster 958, or positioning member, is provided which can be secured to first and second members 930, 931 by bolt 978 at any of a plurality of positions. Depth adjuster 958 includes two slots 962 traversed by bolt 978 and a depth stop surface 960. Depth adjuster 958 can be moved proximally or distally to set a desired insertion depth of jaws 980, 981, and thereby fluid conduits 918, 919, into the nostrils of the animal. Depth stop surface 960 contacts the nose of the animal at the desired insertion depth to stop forward, or distal, movement of intranasal administration device 900.

First and second jaws 980, 981 extend distally from actuation mechanism 928 and include, at the distal ends thereof, septum interference members 990, 991 configured to form a pinch point 996 when first and second jaws 980, 981 are closed. Jaws 980, 981, in the present embodiment, comprise straight jaw portions 988, 989 coupled to first and second arms 932, 933 and curved jaw portions 984, 985; and septum interference members 990, 991. In the present embodiment, curved jaw portions 984, 985 curve outwardly and then inwardly, thus extend on both sides of the centerline of straight portions 988, 989. Septum interference members 990, 991 have blunted edges to prevent tissue trauma and are curved and substantially flat perpendicularly to the curvature. As shown, septum interference members 990, 991 are about twice as wide as they are thick, to enable clamping while permitting substantially unimpeded breathing by the animal. The flat profile increases the ability of the animal to breathe. The thickness of septum interference members 990, 991 (across the flat profile) is sufficient to prevent tissue trauma at pinch point 996. These characteristics may depend on the age and weight of the animal, and the weight of intranasal administration device 900, which collectively determine the minimum biasing force necessary to clamp intranasal administration device 900 onto the nasal septum.

Figure 9:
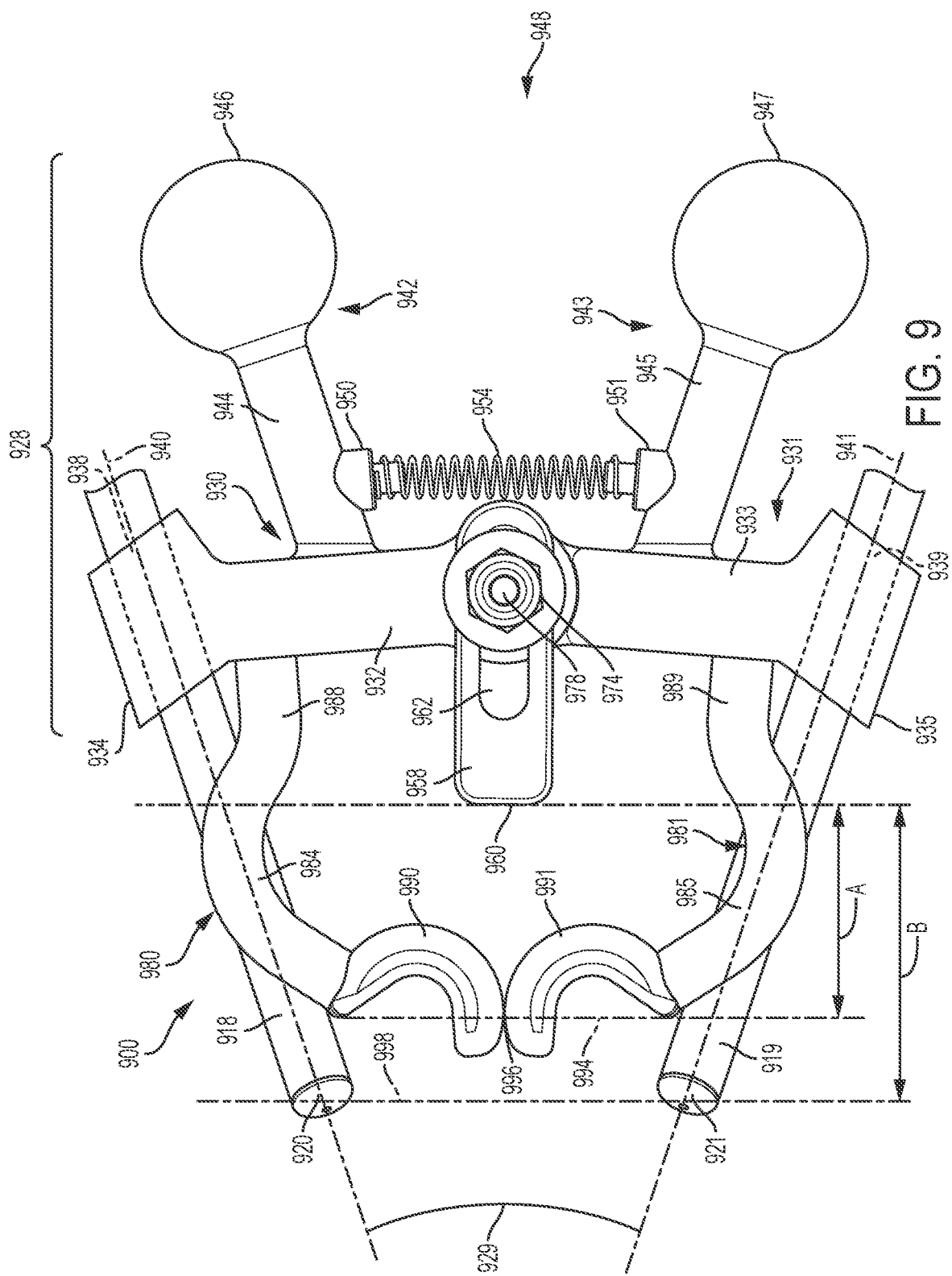

As illustrated in FIG. 9, fluid conduits 918, 919 are supported by first and second members 930 and 931 via elongate fluid conduit support openings 938, 939. The distal ends of fluid conduits 918, 919 extend past pinch point 996, and thereby nasal passage nozzles 920, 921 are also positioned distally of septum interference members 990, 991 The insertion depth of the fluid conduits may be adjusted by sliding fluid conduits 918, 919 within elongate fluid conduit support openings 938, 939 or by cutting fluid conduits 918, 919 to achieve an appropriate insertion depth. A distance A is defined by the longitudinal distance between depth stop surface 960 and pinch point 996. A transverse line 994 passing through pinch point 996 is shown to better illustrate distance A. A longitudinal distance B is defined by depth stop surface 960 and the distal ends of fluid conduits 918, 919. A transverse line 998 passing through nasal passage nozzles 920, 921 is shown to better illustrate distance B. In some embodiments, distance A is between 1 and 3 inches, more preferably between 1½ and 2½ inches, for a bovine animal weighing between 400 and 700 pounds, and distance B is between 2 and 6 inches, more preferably between 3 and 5 inches, and even more preferably between 3½ and 4½ inches. Elongate fluid conduit support openings 938 and 939 are disposed at least partially below jaws 980, 981 to facilitate alignment of the fluid conduits with the ventral meatus. In addition to providing support, elongate fluid conduit support openings 938 and 939 establish an angle between the fluid conduits, which changes as the device is opened or closed. In some embodiments, the angle comprises between 35 and 60 degrees when the jaws are in contact with each other, as shown in FIG. 9. In some embodiments, the angle comprises between about 40 and 50 degrees when the jaws are in contact with each other. Fluid conduits 918, 919 and nasal passage nozzles 920, 921 are designed for insertion into the right and left ventral meatus of the nasal passages at an angle/orientation that is substantially aligned with a longitudinal direction of the ventral meatus. This orientation reduces tissue trauma and aids in insertion depth and animal acceptance.

Figure 11:
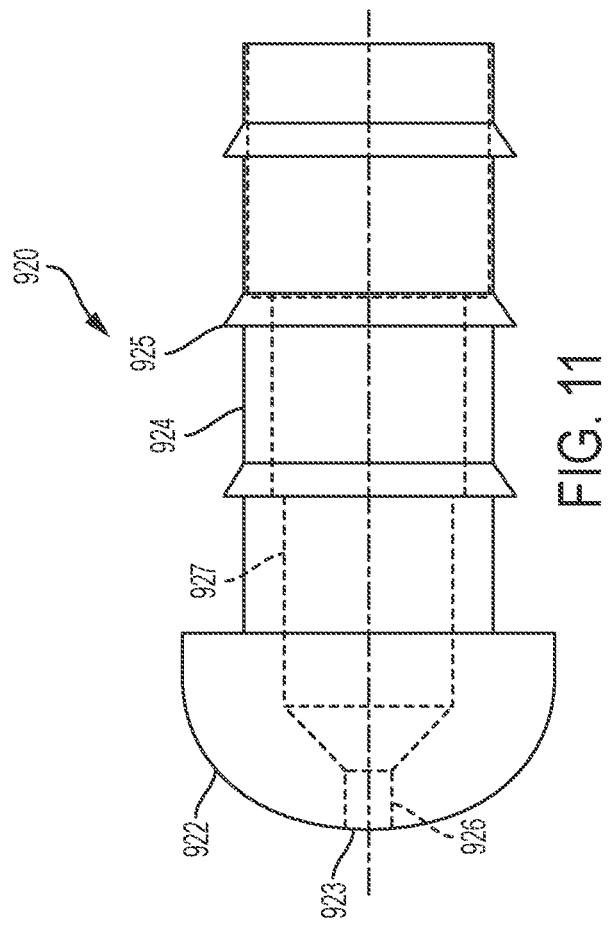
FIGS. 10 and 11 are perspective and side views of a nasal passage nozzle comprised in an intranasal administration device, in accordance with a further example of the present disclosure.
Figure 10:
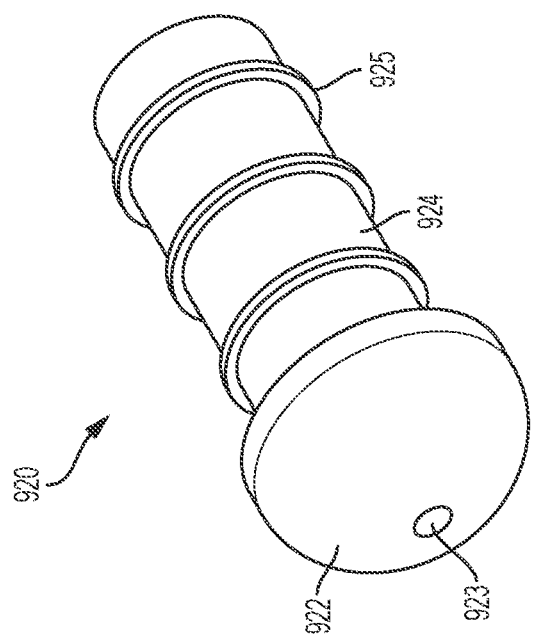

FIGS. 10 and 11 are perspective and side views of an embodiment of nasal passage nozzle 920, which is identical to nasal passage nozzle 921. Nasal passage nozzle 920 comprises a head 922 connected to a body 924 having a plurality of ribs 925 configured to secure body 924 within the distal end of fluid conduit 918. Head 922 has an external diameter perpendicular to its longitudinal axis which is substantially equal to the diameter of fluid conduit 918. Head 922 may be semi-spherically shaped. In various examples, the diameter of head 922 is between about 0.300 and 0.450 inches, more preferably between about 0.350 and 0.400 inches, and even more preferably between about 0.370 and 0.380 inches. In some embodiments, body 924 has a diameter between about 0.220 and 0.280 inches, and more preferably between about 0.240 and 0.260 inches. As shown in FIG. 11, nasal passage nozzle 920 further comprises a distal cavity 926 with an orifice 923 at its distal end and a medial cavity 927 having a diameter larger than the diameter of distal cavity 926 with conical transition portion therebetween configured to constrict and stabilize the fluid prior to discharge. As shown, distal cavity 926 is cylindrical. It is estimated that fluid discharged through distal cavity 926 exhibits a full cone spray pattern with a round impact area and uniform distribution, and a spray angle of 55 degrees at 29 pounds per square inch (PSI) of pressure, discharging at said pressure 0.13 gallons per minute (GPM) of fluid with a mean drop diameter of 270 microns. As shown, distal cavity 926 has a cylindrical shape. In other embodiments other shapes may be used to produce spray patterns with different impact areas. For example, an elliptical pattern may be desired. The diameter of distal cavity 926 may be changed to increase the discharge capacity above or below 0.13 GPM. In some embodiments, the discharge capacity is between about 0.12 and 0.26 GPM. In some embodiments, the discharge pressure is between about 20 and 25 PSI at the nozzle opening of the nasal passage nozzle. In some embodiments, the mean drop diameter is between about 260 and 300 microns. The nasal passage nozzle may be fitted with a whirler. Exemplary whirlers comprise X shaped, disc-shaped and spiral-shaped whirlers, which are configured to distribute the fluid evenly to produce the full cone spray shape.

A pump is fluidly coupled between a reservoir for the fluid and the intranasal administration device. The pump may be controlled to change the pressure and discharge time, which may be configured to generate a dosing volume of between about 30 and 35 milliliters of fluid at nozzle pressure of between about 20 to 25 PSI with a fluid having a density similar to the density of water. Larger or smaller dosing volumes would be appropriate for differently sized animals. A density similar to the density of water may range between 0.8 and 1.2 g/cm$^3$.

Figure 13:
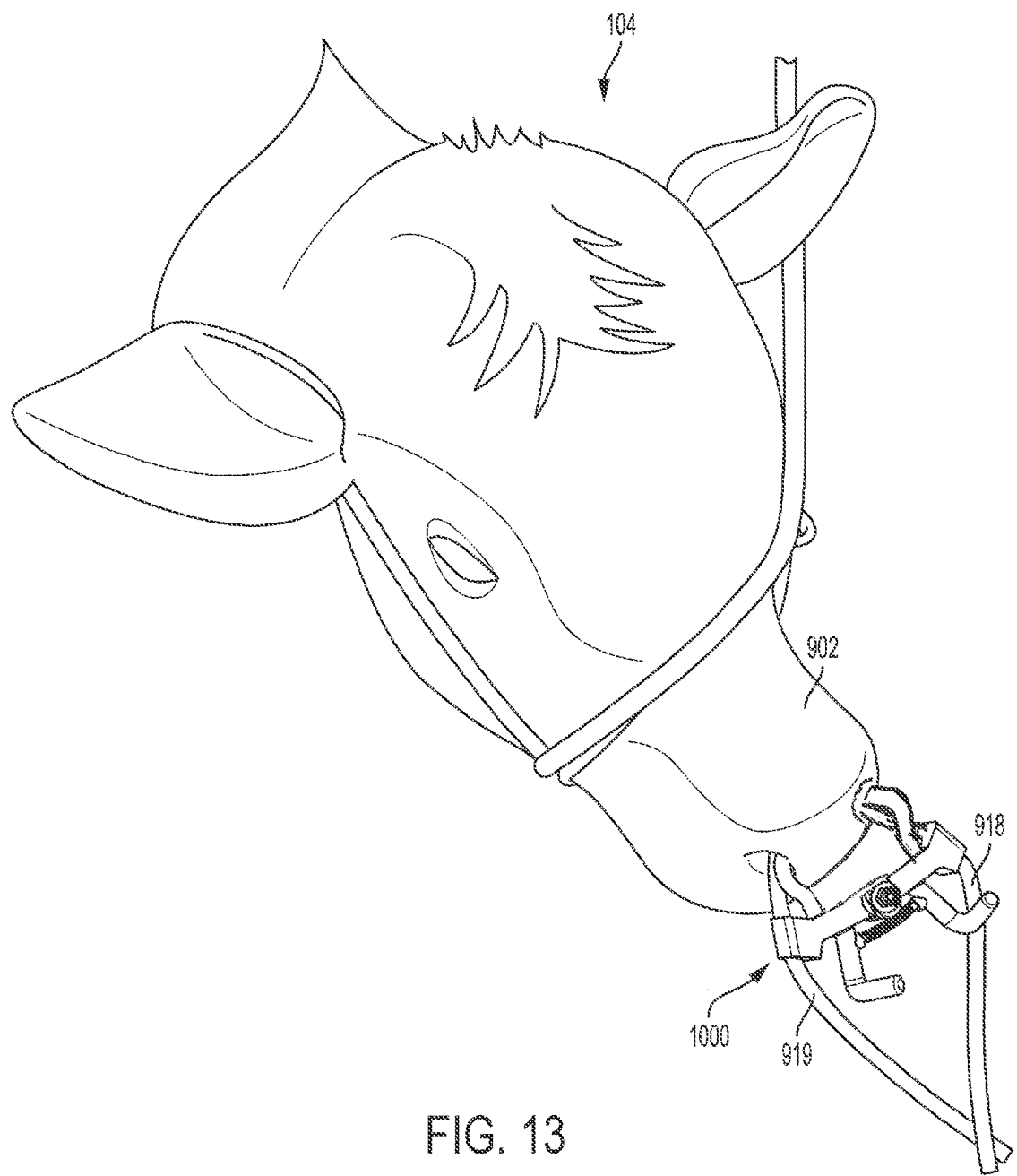
FIG. 13 is a perspective view of the head of an animal showing an intranasal administration device coupled to the nose of the animal, in accordance with yet another example of the present disclosure.
Figure 14:
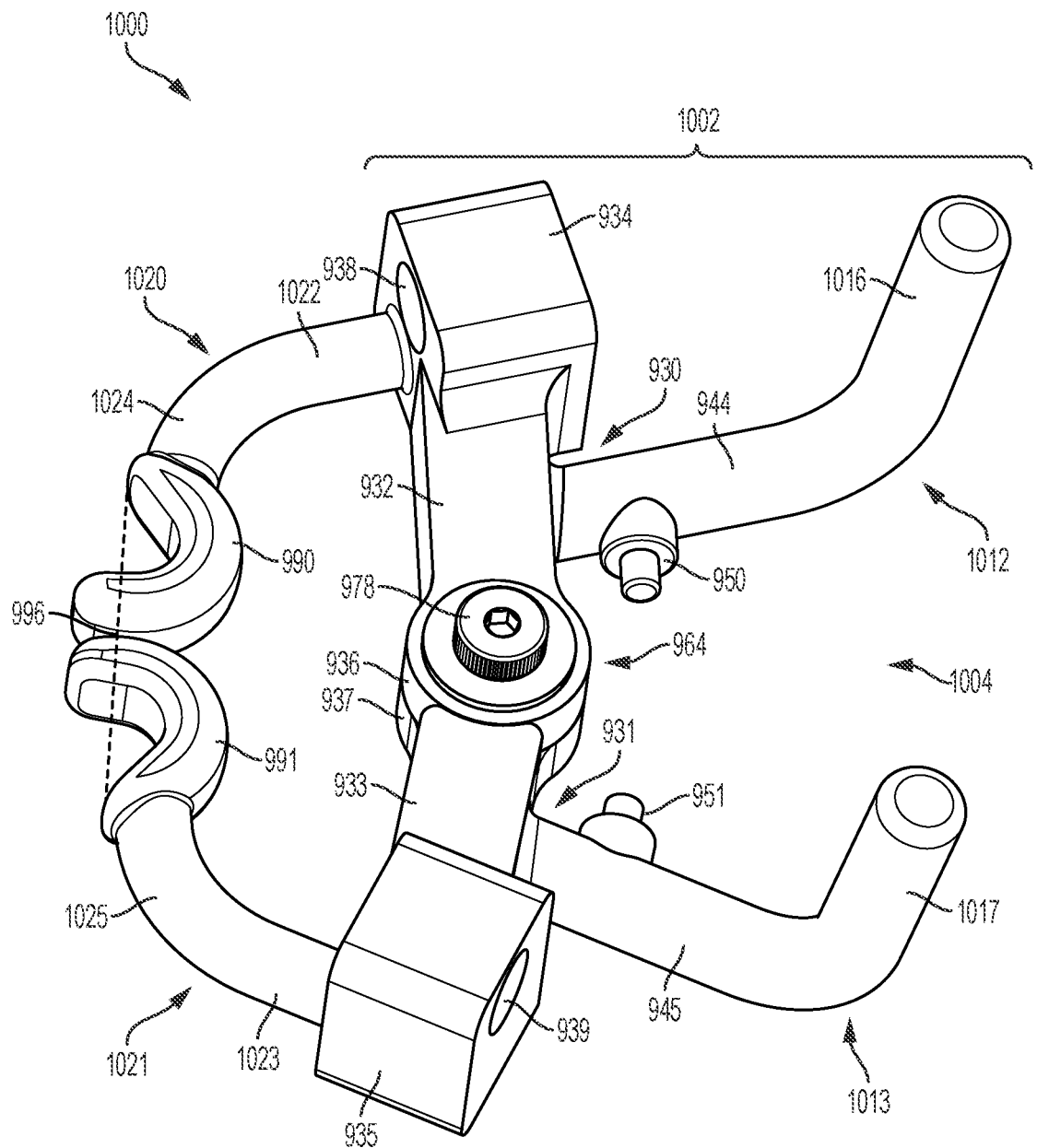
FIGS. 14 to 16 are perspective, top, and rear views of the intranasal administration device depicted in FIG. 13.
Figure 15:
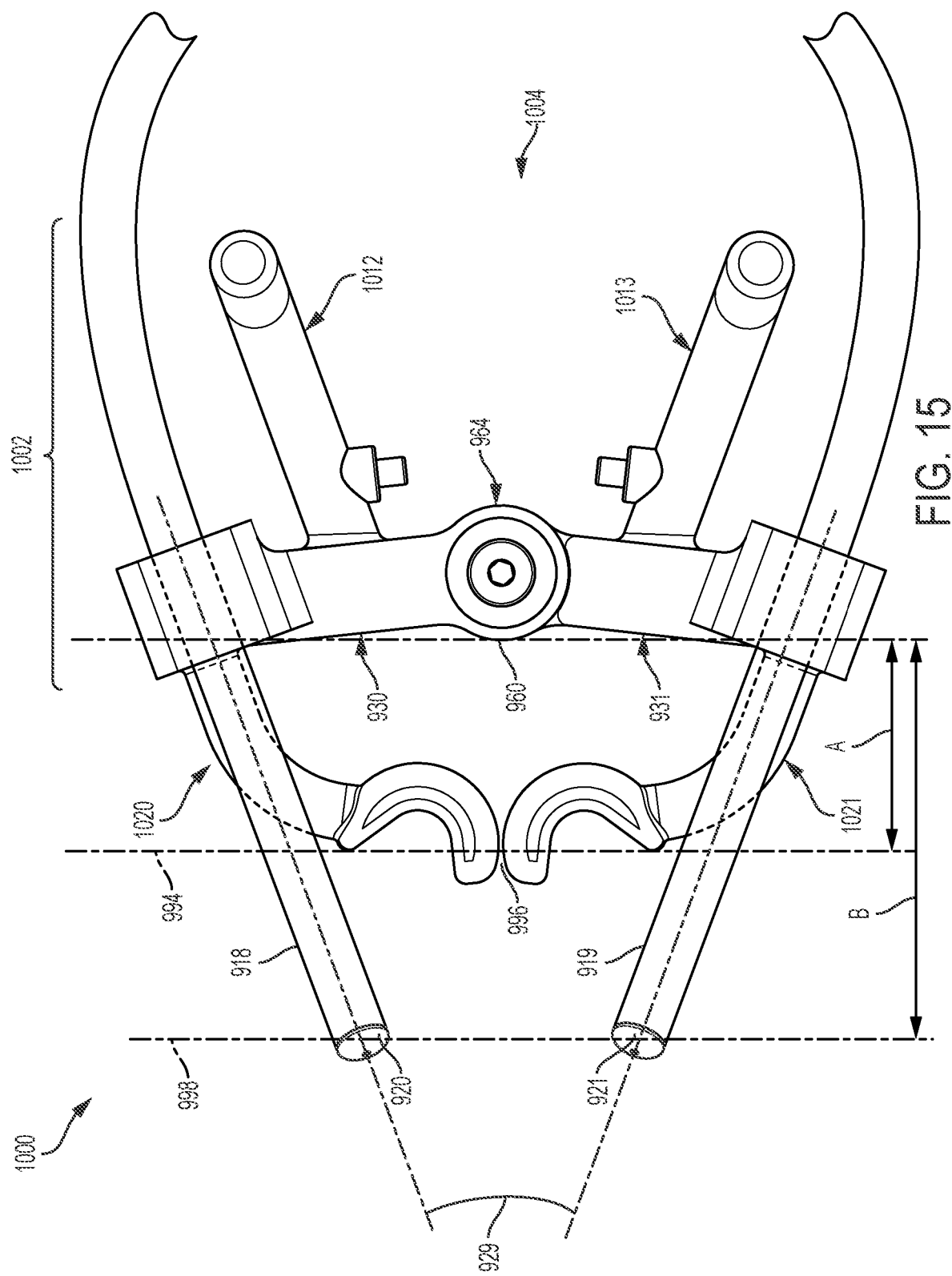
Figure 16:
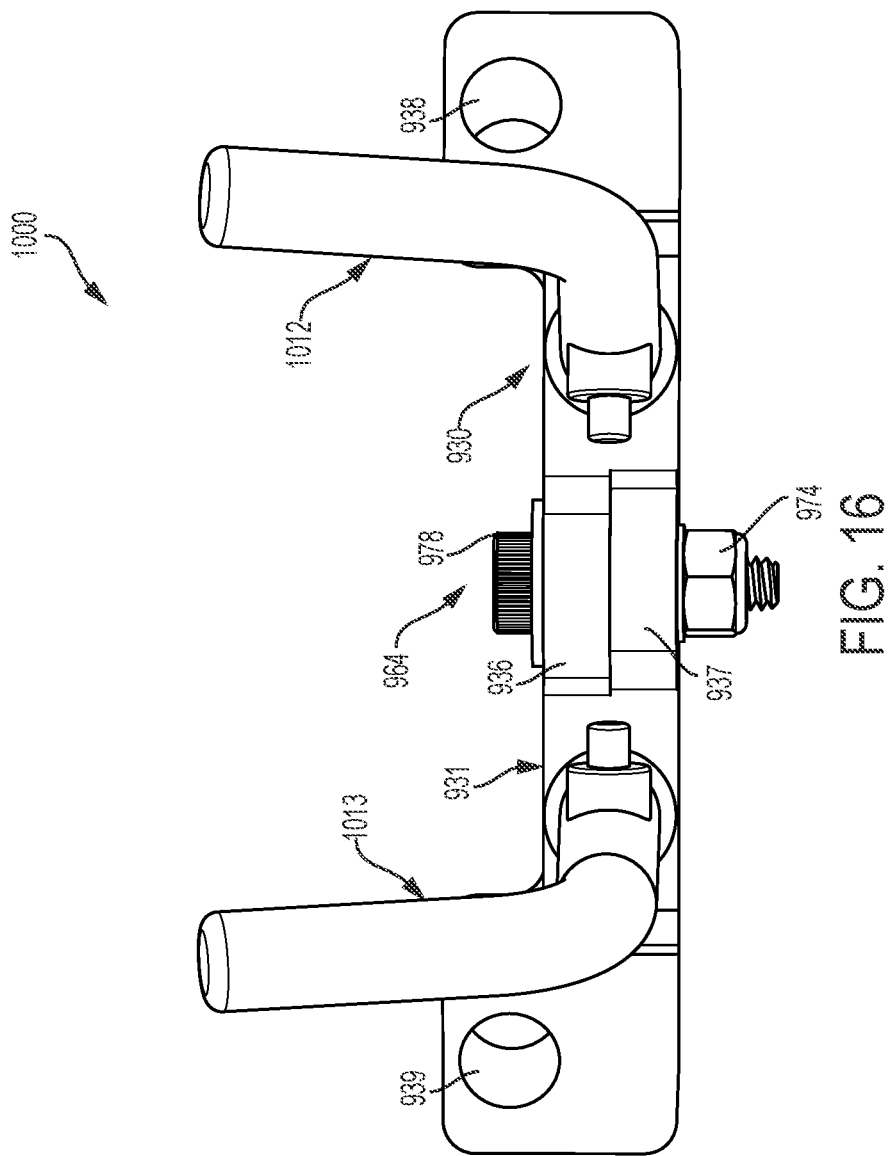

FIG. 13 is a perspective view of the head of animal 104 illustrating another embodiment of an intranasal administration device, denoted by numeral 1000, which is illustrated in FIGS. 14 to 16. Intranasal administration device 1000 differs from intranasal administration devices 101, 201, 301, 401, 501, 701, 801, and 900 in that the jaws and the handle have different characteristics. Intranasal administration device 1000 comprises an actuation mechanism 928 including a handle 1004, and jaws 1020, 1021. Handle 1004 comprises first and second handle members 1012, 1013. First handle member 1012 extends from first arm 932 and includes first handle portion 944 and a second handle portion 1016. Second handle member 1013 extends from second arm 933 and includes a first handle portion 945 and a second handle portion 1017. Second handle portions 1016, 1017 are transverse bars that extend from first handle portions 944, 945 and which may have any desirable length sufficient to enable operation of handle 1004 by permitting the user to grip second portions 1016, 1017 without interference from fluid conduits 918, 919. Second handle portions 1016, 1017 may face upward or downward, depending on the relative position of the pump system, so as to limit interference with the fluid conduits. Handle 1004 is also referred to as a user interface. Jaws 1020, 1021 include straight jaw portions 1022, 1023 and curved jaw portions 1024, 1025. By contrast with intranasal administration device 900, jaws 1020, 1021 curve inwardly and no part thereof extends outside the longitudinal axis of straight jaw portions 1022, 1023. The curvature of the jaws can interfere with the nostrils of the animal and can also prevent or interfere with breathing of the animal.

In one embodiment, a dosing volume of between about 30 and 35 milliliters of fluid at a nozzle tip discharge pressure of between about 20 to 25 PSI was delivered with intranasal delivery device 900 to a bovine animal weighing between 400 and 700 lbs. The fluid contained a colored dye and had a density similar to the density of water. Upon dissection of the head of the animal it was observed that the nasopharynx of the animal was substantially coated.

In some embodiments, a method to deliver a fluid intranasally to a veterinary subject, the method comprises opening the jaws of an intranasal administration device 900, 1000; inserting the jaws into the nostrils of the veterinary subject while inserting the distal ends of fluid conduits medially and posteriorly into the ventral meatus; clamping the nasal septum of the veterinary subject with the jaws; and discharging a fluid through the fluid conduits.

Inserting the jaws and the fluid conduits into the nostrils of the veterinary subject comprises inserting the fluid conduits through flow constrictions formed by the alar folds and the basal folds of the veterinary subject. Inserting the jaws and the fluid conduits into the nostrils of the veterinary subject may comprise moving the intranasal administration device toward the veterinary subject until a depth stop surface of the intranasal administration device contacts the nose of the veterinary subject.

The fluid may comprise a nitric oxide releasing solution or a nitric oxide gas or a combination of the nitric oxide releasing solution and the nitric oxide gas. After delivery of the fluid, the jaws are unclamped and the intranasal administration device is removed.

Embodiments of the invention have been described including an actuation mechanism, two jaws, and two fluid conduits. In various embodiments, the actuation mechanism may comprise a ratchet mechanism including a gear and a pawl mounted on a base, and a release lever to release the pawl from the gear, whereby the first and second members are brought together by the user to clamp the device and movement of the release lever enables separation of the first and second members to release the device. Other actuation mechanisms known in the art may also be used.

The following examples pertain to further embodiments:

In one example, an animal intranasal administration device can comprise a nasal passage nozzle for a nostril configured to receive fluid from a fluid source; a support structure opposing the nasal passage nozzle; and a biasing mechanism to bias the nasal passage nozzle and the support structure toward a septum such that the device is secured in place about the septum during administration of the fluid into a nasal passage.

In on example, the support structure comprises a second nasal passage nozzle.

In one example, the biasing mechanism comprises a spring to bias the nasal passage nozzles toward the septum.

In one example, the animal intranasal administration device can further comprise a support member having a first support member portion and a second support member portion each in support of a nozzle, wherein the first support member portion and the second support member portion are movable relative to one another by the biasing mechanism.

In one example, the biasing mechanism comprises resilient flexibility of at least one of the first support member portion and the second support member portion.

In one example, the first and second support member portions are pivotally coupled to one another.

In one example, the animal intranasal administration device can further comprise a positioning member configured to contact a tip of the septum to facilitate and maintain proper positioning of nasal passage nozzles.

In one example, the nasal passage nozzles are oriented to align nozzle openings with nasal passages when the device is engaged with the septum.

In one example, the nasal passage nozzles are configured to direct fluid into the nasal passages past nasal folds.

In one example, the nasal passage nozzles are configured to extend into the nostrils beyond the nasal folds.

In one example, the nasal folds comprise at least one of an alar fold, a basal fold, and a straight fold.

In one example, the animal intranasal administration device can further comprise a fluid distribution manifold fluidly coupled to the nasal passage nozzles, the fluid distribution manifold having an inlet port to receive fluid from the fluid source and outlet ports to distribute fluid to the nasal passage nozzles.

In one example, the animal intranasal administration device can further comprise a septum interface portion associated with each of the nasal passage nozzles to interface with the septum and position the nasal passage nozzles to facilitate directing fluid into the nasal passages.

In one example, the animal intranasal administration device can further comprise a user interface to facilitate movement of the nasal passage nozzles by a user in a direction opposite a biasing direction.

In one example, the fluid is selected from the group consisting of: a liquid, a gas, a gel, or a combination thereof.

In one example, an animal intranasal administration device can comprise a support member having a first support member portion and a second support member portion, a first nasal passage nozzle, and a second nasal passage nozzle, wherein the first support member portion and the second support member portion are movable relative to one another to position the first and second nasal passage nozzles at least partially within nostrils of an animal about a septum and such that fluid is directed into nasal passages of the animal.

In one example, the first and second support member portions are biased toward a secured position about the septum.

In one example, the animal intranasal administration device can further comprise a spring to bias the first and second support member portions toward the secured position.

In one example, at least one of the first and second support member portions is resiliently flexible to bias the at least one of the first and second support member portions toward the secured position.

In one example, the support member is configured to provide clearance about a tip of the septum.

In one example, the first and second support member portions comprise arcuate configurations to provide clearance about the tip of the septum.

In one example, the first and second nasal passage nozzles are oriented to align nozzle openings with the nasal passages of the animal when the device is engaged with the animal.

In one example, the fluid conduits are external to the support member.

In one example, at least one of the first and second support member portions comprises at least a portion of the conduit. The distal ends of the conduits thus protrude from the first and second support member portions and are not supported therewith.

In one example, the user interface comprises a first user interface portion coupled to the first support member portion, and a second user interface portion coupled to the second support member portion, and wherein the first and second user interface portions are movable relative to one another to facilitate movement of the first and second support member portions relative to one another.

In one example, an animal intranasal administration system can comprise any of the animal intranasal administration devices described herein. The animal intranasal administration system can further comprise a pump operable to deliver fluid from the fluid source to the first and second nasal passage nozzles. The pump is configured to pump at least one of a liquid and a gas.

In one example, a pump of an animal intranasal administration system comprises a motorized pump, a hand pump, or a combination thereof.

In one example, the fluid source comprises activated nitric oxide releasing solution.

In one example, the fluid source comprises inactivated nitric oxide releasing solution.

In one example, the fluid source comprises a container with the inactivated nitric oxide releasing solution disposed therein, and wherein the inactivated nitric oxide releasing solution is activatable within the container.

In one example, fluid is configured to dispense from the fluid source to the first and second nasal passage nozzles following activation of the nitric oxide releasing solution due to a pressure in the container resulting from the activation of the nitric oxide releasing solution.

In one example, the animal intranasal administration system can further comprise a cage for containing an activation agent prior to mixing the activation agent with the inactivated nitric oxide releasing solution, wherein the cage is configured to facilitate mixing of the activation agent and the inactivated nitric oxide releasing solution.

In one example, the cage is supported within the container above a bottom of the container.

In one example, the fluid source further comprises an activation agent maintained separate from the inactivated nitric oxide releasing solution and configured to activate the inactivated nitric oxide releasing solution upon mixing.

In one example, the fluid source is fluidly coupled to the first and second nasal passage nozzles via a first conduit associated with the inactivated nitric oxide releasing solution and a second conduit associated with the activation agent.

In one example, the first and second conduits combine prior to the first and second nasal passage nozzles such that mixing of the inactivated nitric oxide releasing solution and the activation agent occurs between the fluid source and the first and second nasal passage nozzles.

In one example, the first and second conduits combine at the first and second nasal passage nozzles such that mixing of the inactivated nitric oxide releasing solution and the activation agent occurs at the first and second nasal passage nozzles.

In one example, the first and second conduits remain separate from the fluid source to the first and second nasal passage nozzles such that mixing of the inactivated nitric oxide releasing solution and the activation agent occurs at the animal.

In one example, the fluid source comprises nitric oxide gas.

In one example, the animal comprises a domesticated animal.

In one example, the domesticated animal comprises a bovine, a swine, an equine, an ovine, or a goat.

In one example, a method of administering a fluid to an animal's nostril can comprise providing an animal intranasal administration device including a support member having a first support member portion and a second support member portion, a first nasal passage nozzle coupled to the first support member portion, and a second nasal passage nozzle coupled to the second support member portion, wherein the first support member portion and the second support member portion are movable relative to one another to secure the first and second nasal passage nozzles at least partially within nostrils of an animal about a septum and such that fluid is directed into nasal passages of the animal, engaging the device with the animal's nostril, and dispensing the fluid from the device and into the animal's nostrils.

In one example, an amount of nitric oxide releasing solution dispensed to the animal is between about 0.1 mL and about 5000 mL.

In one example, the amount of nitric oxide releasing solution dispensed to the animal is between about 10 mL and 1000 mL.

In one example, an amount of nitric oxide releasing solution dispensed to the animal is about 2 mL.

In one example, an amount of nitric oxide releasing solution dispensed to the animal is about 10 mL.

In one example, an amount of nitric oxide releasing solution dispensed to the animal is about 32 mL.

In one example, an amount of nitric oxide releasing solution dispensed to the animal is 160 mL.

In one example, the fluid source comprises inactivated nitric oxide releasing solution.

In one example, the method can further comprise activating the inactivated nitric oxide releasing solution.

In one example, the fluid is dispensed utilizing a gas pressure resulting from the activation of the nitric oxide releasing solution.

In one example, activating the inactivated nitric oxide releasing solution occurs prior to dispensing the fluid from the device and into the animal's nostril.

In one example, activating the inactivated nitric oxide releasing solution occurs when dispensing the fluid from the device and into the animal's nostril.

In one example, activating the inactivated nitric oxide releasing solution occurs after dispensing the fluid from the device and into the animal's nostril.

It is noted that no specific order is required in the methods disclosed herein, though generally in some embodiments, the method steps can be carried out sequentially.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An intranasal administration device for a veterinary subject, comprising:
   a first support member portion including a septum interface portion sized for insertion into a nasal passage of the veterinary subject;
   an actuation mechanism comprising a first member pivotally coupled to a second member to allow the first member to pivot relative to the second member, the first member connected to the first support member portion; and
   a fluid conduit having a distal end opposite a supported end, the distal end sized for insertion into the nasal passage of the veterinary subject, the fluid conduit being flexible and sized and configured to receive fluid from a fluid source and discharge the fluid through the distal end into the nasal passage, the distal end of the fluid conduit being unsupported and movable relative to the septum interface portion.

2. The intranasal administration device of claim 1, wherein the first support member portion includes a first nasal passage nozzle, further comprising a second support member portion including a second septum interface portion, a second fluid conduit having a second distal end, and a second nasal passage nozzle supported by the second distal end of the second fluid conduit.

3. The intranasal administration device of claim 2, wherein the actuation mechanism comprises elongate fluid conduit support openings through which the fluid conduit and the second fluid conduit, respectively, pass, and wherein the centerlines of the elongate fluid conduit support openings form an angle of between about 40 and 60 degrees when the septum interface portion and the second septum interface portion contact each other.

4. The intranasal administration device of claim 3, wherein a distance between the elongate fluid conduit support openings is between about 2 and 5 inches.

5. The intranasal administration device of claim 4, wherein the distance between the elongate fluid conduit support openings is between about 3 and 4 inches.

6. The intranasal administration device of claim 2, wherein the fluid conduits are formed of a flexible material and are configured to self-align with the nasal passages of the veterinary subject during insertion into the nasal passages.

7. The intranasal administration device of claim 1, wherein the actuation mechanism comprises a biasing mechanism providing a biasing force to bias the first support member portion toward the nasal septum of the veterinary subject and clamp the intranasal administration device about the nasal septum.

8. The intranasal administration device of claim 7, wherein the actuation mechanism comprises a user interface operable by a user to overcome the biasing force and thereby unclamp the intranasal administration device from the nasal septum.

9. The intranasal administration device of claim 1, wherein the actuation mechanism comprises a depth stop surface configured to contact the nose of the veterinary subject and thereby determine an insertion depth of the distal end of the fluid conduit.

10. The intranasal administration device of claim 9, wherein the insertion depth for a bovine animal weighing between 400 and 700 pounds is at least 3.0 inches.

11. The intranasal administration device of claim 1, wherein the actuation mechanism comprises two elongate fluid conduit support openings, and wherein a distance between the two elongate fluid conduit support openings is between about 3 and 4 inches.

12. The intranasal administration device of claim 1, wherein the distal end of the fluid conduit is sized to extend into the nostril of the veterinary subject at least one inch past the septum interface portion.

13. A method to deliver a fluid intranasally to a veterinary subject, the method comprising:
opening jaws of an intranasal administration device, the intranasal administration device comprising an actuation mechanism comprising a first member pivotally coupled to a second member to allow the first member to pivot relative to the second member, the jaws comprising a first jaw and a second jaw, the first member supporting the first jaw and the second member supporting the second jaw, the intranasal administration device further comprising fluid conduits having distal ends that are unsupported and movable relative to septum interface portions of the jaws;
inserting the jaws and the fluid conduits into the nostrils of the veterinary subject;
clamping the nasal septum of the veterinary subject with the jaws to retain the fluid conduits in the nose of the veterinary subject; and
discharging a fluid through the fluid conduits.

14. The method of claim 13, wherein inserting the jaws and the fluid conduits into the nostrils of the veterinary subject comprises inserting the fluid conduits through flow constrictions formed by the alar folds and the basal folds of the veterinary subject.

15. The method of claim 13, wherein inserting the jaws and the fluid conduits into the nostrils of the veterinary subject comprises inserting the fluid conduits into the ventral meatus of the veterinary subject.

16. The method of claim 13, wherein inserting the jaws and the fluid conduits into the nostrils of the veterinary subject comprises moving the intranasal administration device toward the veterinary subject until a depth stop surface of the intranasal administration device contacts the nose of the veterinary subject.

17. The method of claim 13, wherein the fluid conduits are formed of a flexible material and are configured to bend along the nasal septum as the distal ends of the jaws approach each other.

18. The method of claim 13, wherein the fluid comprises a nitric oxide releasing solution or a nitric oxide gas or a combination of the nitric oxide releasing solution and the nitric oxide gas.

19. An intranasal administration device comprising:
a first member pivotally coupled to a second member to allow the first member to pivot relative to the second member, each of the first member and the second member including:
an arm, wherein the arm of the first member is pivotally coupled to the arm of the second member; and
a handle portion coupled to and extending proximally from the arm;
jaws coupled to and extending distally from the arms and having distal ends, wherein the distal end of the jaw of the first member and the distal end of the jaw of the second member are configured to clamp the nasal septum of a veterinary subject;
a fluid conduit supported by the first member and having a distal end detached from the distal end of the jaw of the first member; and
a second fluid conduit supported by the second member and having a distal end detached from the distal end of the jaw of the second member,
wherein the first fluid conduit and the second fluid conduit are sized to extend past a flow constriction formed by the alar folds and the basal folds of the veterinary subject, when the intranasal administration device is clamped to the nasal septum, to deliver a fluid into the veterinary subject.

20. The intranasal administration device of claim 19, further comprising nasal passage nozzles disposed at the distal ends of the first fluid conduit and the second fluid conduit and configured to discharge the fluid in a conical pattern.

21. The intranasal administration device of claim 20, wherein the distal ends of the first and second fluid conduits are configured to bend by contact with tissue of the veterinary subject.

22. The intranasal administration device of claim 21, wherein bending of the distal ends of the first and second fluid conduits moves the nasal passage nozzles away from the septum interface portions.

23. The intranasal administration device of claim 19, wherein each jaw comprises a straight portion extending from the arm, a curved portion extending from the straight portion, and a septum interface portion extending from the curved portion.

24. The intranasal administration device of claim 23, wherein the septum interface portions of the jaws comprise widths measured perpendicularly to the nasal septum and thicknesses measured perpendicularly to the widths, wherein the widths are at least twice the thicknesses.

25. The intranasal administration device of claim 23, wherein the septum interface portions are curved and substantially flat perpendicularly to the curvature.

26. The intranasal administration device of claim 19, wherein the first fluid conduit and the second fluid conduit are sized to extend into the ventral meatus when the intranasal administration device is clamped to the nasal septum.

27. The intranasal administration device of claim 19, further comprising a pump configured to discharge a dosing volume of fluid of between about 30 and 35 milliliters at a nozzle tip discharge pressure of between about 20 and 25 pounds per square inch.

28. The intranasal administration device of claim 19, wherein the fluid conduits are supported by the first member and the second member and are unsupported distally of the first member and the second member.

* * * * *